United States Patent [19]

Hickey et al.

[11] Patent Number: 5,599,809
[45] Date of Patent: Feb. 4, 1997

[54] METHOD FOR IMPROVING REPRODUCTIVE EFFICIENCY IN FARM ANIMALS

[75] Inventors: Gerard J. Hickey, Westfield, N.J.; Douglas J. Pettibone, Chalfont, Pa.

[73] Assignee: Merck & Co., Inc., Rahway, N.J.

[21] Appl. No.: 314,840

[22] Filed: Sep. 29, 1994

[51] Int. Cl.$^6$ .......................... A61K 31/495; A01N 43/58
[52] U.S. Cl. .................. 514/212; 514/226.8; 514/235.8; 514/747; 514/249; 514/250; 514/252; 514/253; 514/254; 514/255
[58] Field of Search .......................... 514/252, 253, 514/254, 255, 247, 249, 250, 235.8, 226.8, 212

[56] References Cited

FOREIGN PATENT DOCUMENTS 0532097  3/1993  European Pat. Off. .
614894   9/1994  European Pat. Off. .

OTHER PUBLICATIONS

Flint, A. P. F.; Sheldrick, E. L.; J. Reprod. Fert., 76:831–839 (1986), entitled Ovarian oxytocin and the maternal recognition of pregnancy, Dec. 1986.

Flint, A. P. F. et al.; J. Reprod. Fert., Suppl. 45:53–58 (1992), entitled Role of the oxytocin receptor in the choice between cyclicity and gestation in ruminants, Dec. 1992.

Jenkins, G.; J. Reprod. Fert., Suppl. 45:97–111(1992), entitled Oxytocin and prostaglandin interactions in pregnancy and at parturition., Dec. 1992.

Jenner, L. J., et al.; J. Reprod. Fert., 91:49–58 (1991), entitled Uterine oxytocin receptors in cyclic and pregnant cows. Dec. 1991.

Plante et al., J. Reprod. Fert., 93, 375–384 (1991), entitled Alteration of oestrous cycle length, ovarian function and oxytocin–induced release of prostaglandin F–2a by intrauterine and intramuscular administration of recombinant bovine interferon-a to cows Dec. 1991.

Cooke et al., J. Reprod. Fert. 75, 63–68 (1985), entitled Suppression of prostaglandin F–2a release and delay of luteolysis after active immunization against oxytocin in the goat. Dec. 1985.

Bazer et al., J. Reprod. Fert., Suppl. 37, 85–89 (1989) entitled Comparative aspects of maternal recognition of pregnancy between sheep and pigs Dec. 1989.

Mirando et al., Biology of Reproduction 42, 98–105 (1990) entitled Oxytocin–stimulated inositol phosphate turnover inendometrium of ewes is influenced by stage of the estrous cycle, pregnancy, and intrauterione infusion of ovine conceptus secretory proteins Dec. 1990.

Graham Jenkin, Reproductive. Fertil. Dev., Interaction Between Oxytocin and Prostaglandin F2 Alpha During Luteal Regression and Early Pregnancy in Sheep, vol. 4, No. 3, Dec. 1992.

K. M. Burgess et al., Biology of Reproduction, Effect of Oxytocin and Estradiol on Uterine Prostaglandin Releases in Nonpregnant and Early–Pregnant Ewes, vol. 42, pp. 822–833 Dec. 1990.

*Primary Examiner*—James J. Seidleck
*Assistant Examiner*—John M. Cooney, Jr.
*Attorney, Agent, or Firm*—Melvin Winokur; William H. Nicholson; Mary A. Appollina

[57] ABSTRACT

Oxytocin receptor antagonists of the formula

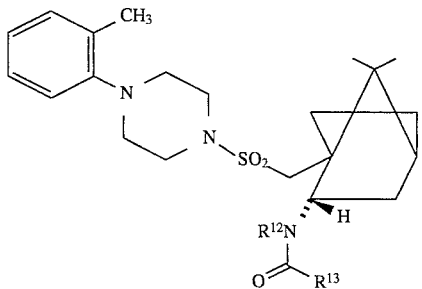

wherein $R^{12}$ is hydrogen, alkoxycarbonyl or unsubstituted of substituted alkyl; $R^{13}$ is hydrogen, alkoxyl, aralkoxyl, alkoxycarbonyl, alkoxycarbonylamino, unsubstituted or substituted cycloalkyl, unsubstituted or substituted phenyl, unsubstituted or substituted amino, unsubstituted or substituted rings of the formulae

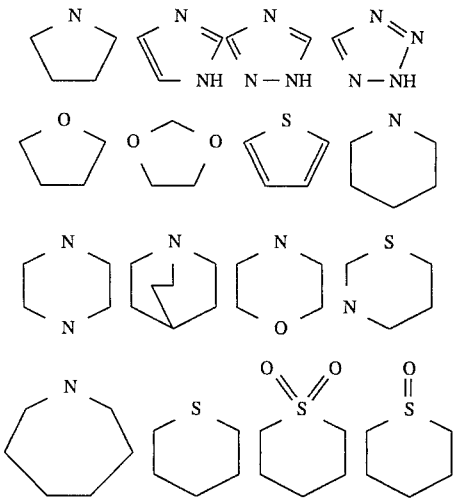

unsubstituted or substituted alkyl, and the pharmaceutically acceptable salts thereof, are useful for increasing fertility rates, embryonic survival and overall reproductive efficiency in farm animals.

36 Claims, No Drawings

METHOD FOR IMPROVING REPRODUCTIVE EFFICIENCY IN FARM ANIMALS

FIELD OF THE INVENTION

The present invention provides a method for increasing reproductive efficiency in farm animals by administration of an oxytocin receptor antagonist compound. More particularly, administration of an oxytocin receptor antagonist of the instant invention for a period of 2 to 3 weeks at the critical period after fertilization increases pregnancy rates in farm animals by enhancing the chances of impregnation through a reduction in embryonic loss. Additionally, the oxytocin receptor antagonists of the present invention are useful for controlling the timing of parturition in farm animals so that delivery occurs during the daylight hours. The oxytocin receptor antagonists of the present invention are also useful for controlling the timing of estrus in farm animals.

BACKGROUND OF THE INVENTION

Oxytocin receptor antagonists have been found to be useful as tocolytic agents. Various oxytocin antagonists have been studied and implemented in the management of conditions such as preterm labor, dysmenorrhea and stopping labor prior to cesarean delivery.

A number of piperazinylcamphorsulfonyl oxytocin receptor antagonists, pharmaceutically acceptable salts thereof, and their use in treating preterm labor, dysmenorrhea and stopping labor prior to cesarean delivery are described in EP Patent Publication No. 532,097, published Mar. 17, 1993. In particular, the compound disclosed in Example 36 of EP 532,097, i.e., 1-((7,7-Dimethyl-2-endo-(2S-amino-4-(methylsulfonyl)butyramido)-bicyclo(2.2.1)-heptan-1-yl-)methanesulfonyl)-4-(2-methylphenyl)piperazine, has been found to be an effective inhibitor-of uterine activity and will hereafter be referred to as Compound A.

In certain farm animals (e.g., sheep, cattle, swine and goats) the beginning of the estrous cycle is typically marked by behavioral estrus when the female animal accepts the male for mating. Ovulation of the ovarian follicle occurs shortly after onset of estrus and cells in the follicle give rise to the corpus luteum. The cells that form the corpus luteum produce progesterone and they also produce oxytocin. The secretion of oxytocin from the corpus luteum and/or pituitary acts on the uterine endometrium to stimulate the secretion of prostaglandins (in particular PGF) which, in ram, causes the regression of the corpus luteum of the ovary. PGF is, therefore, the luteolytic hormone. In the cycling animal (i.e., where mating and fertilization have not occurred), destruction of the corpus luteum removes the source of progesterone which is key to the preparation of the uterus for pregnancy.

The presence of a viable conceptus (i.e., the embryo and its associated membranes) is necessary to prevent the luteolytic process. In fact, the first key signal that the conceptus must produce is the one to prevent regression of the corpus luteum (i.e., the mammal recognition of pregnancy signal). Thus, in the animal where mating and fertilization have occurred, the conceptus secretes a factor that antagonizes the action of oxytocin to induce luteolysis. This results in maintenance of a functioning corpus luteum and the continued secretion of progesterone which is obligatory to the initiation of pregnancy.

Early embryonic loss is a major cause of infertility in farm animals resulting in considerable economic costs. Embryonic deaths claim 30 to 50% of embryos in domestic livestock. Most of this embryonic death loss occurs just prior to or during the period of maternal recognition of pregnancy. Many of the conceptuses are slightly retarded in their development and either do not produce the maternal recognition signal at the appropriate time or do not produce it in adequate amounts. Consequently, leuteolysis is not inhibited and the corpus luteum regresses, resulting in early embryonic loss.

It has now been found that administration of an oxytocin antagonist of the present invention at this critical period after fertilization (i.e., just prior to or during the period of maternal recognition of pregnancy) supplements the natural signal from the conceptus (i.e., maternal recognition of pregnancy) to prolong corpus luteal function. The result is to increase pregnancy rates by enhancing the chances of impregnation through a reduction in embryonic loss.

In addition to the infertility problem caused by embryonic loss in livestock, neonatal morbidity and mortality also result in considerable expense and economic loss to farmers. Approximately 80% of livestock are delivered at night and up to 5 to 10% of newborns die because the deliveries are not monitored properly. Thus, a method of controlling the timing of parturition in livestock to ensure monitoring of the neonates would be highly beneficial, resulting in increased survival rates.

It has now been discovered that oxytocin antagonists of the present invention can be used in livestock to control the Compound A

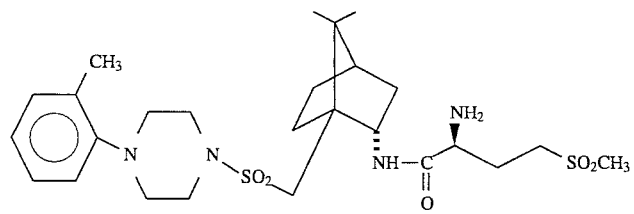

timing and delivery of neonates to the daytime, thereby allowing for monitoring of the neonates and enhanced survival rates.

Additionally, synchronization of estrus among a group of farm animals would increase the ease and efficiency of farm management resulting in savings of both time and cost. For example, the synchronization of estrus among a herd of cows would allow for mating or artificial insemination of the entire herd on the same day. Moreover, by fertilizing the entire herd on the same day, the cows would all be expected to deliver the neonates on or about the same day. Thus, a farmer would realize time and cost savings during breeding and the resulting births by synchronizing estrus of the entire herd.

It has now been found that administration of an oxytocin antagonist of the instant invention can be used to control the timing of estrus in a cycling animal by preventing luteal regression; by using an oxytocin antagonist to prevent luteal regression and delay estrus, a farmer will be able to synchronize estrus among a group of farm animals, thereby easing farm management.

SUMMARY OF THE INVENTION

The present invention is directed to a method of increasing fertility and embryonic survival in a farm animal, comprising administering to the farm animal a pharmacologically effective amount of a compound of formula I

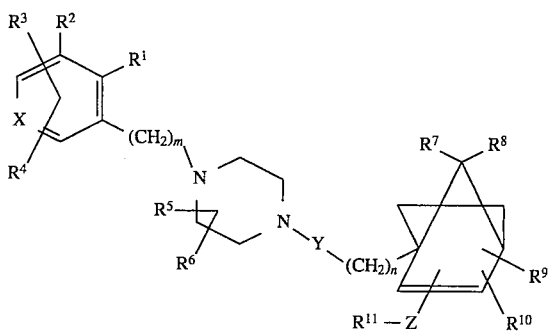

wherein
X is
(1) C or
(2) N;
Y is
(1) carbonyl or
(2) sulfonyl;
Z is an optional substituent that, when present, is substituted or unsubstituted alkyl where said substituent is carboxyl;
$R^1$ is
(1) hydrogen,
(2) alkyl or
(3) $NH_2$;
$R^2$ is
(1) hydrogen, or
$R^1$ and $R^2$ together are bridged alkyl of three or four methylenes so as to form either

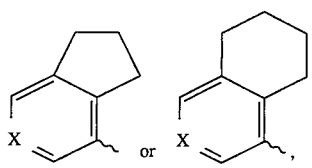

respectively;
$R^3$ and $R^4$ are independently one or more of
(1) hydrogen,
(2) halogen,
(3) alkylsulfonyl,
(4) alkoxy or
(5) unsubstituted or substituted alkyl wherein said substituent is hydroxyl, alkoxyl, alkylsulfonyl, amino, alkylamino or dialkylamino;
$R^5$ and $R^6$ are independently selected from
(1) hydrogen,
(2) alkyl,
(3) substituted alkyl where said substituent is amino, hydroxyl, alkoxyl, alkylsulfonyl, arylsulfonyl, alkylamino or dialkylamino,
(4) phenylalkyl or (5) oxo;
$R^7$ and $R^8$ are independently one or more of
(1) hydrogen,
(2) alkyl or
(3) joined together to form unsubstituted or substituted cycloalkyl where said substituent is hydroxy or hydroxyalkyl;
$R^9$ and $R^{10}$ are independently selected from
(1) hydrogen,
(2) hydroxyl,
(3) halogen,
(4) oximino,
(5) methyl,
(6) carboxyl,
(7) oxo,
(8) alkoxycarbonyl,
(9) alkylcarbonyloxy,
(10) alkoxycarbonylalkoxy,
(11) sulfonyloxy,
(12) trihaloalkylsulfonyloxo or
(13) unsubstituted or substituted amino where said substituent is one or more of alkyl, carboxyalkyl or alkoxycarbonylalkyl; or
$R^9$ and $R^{10}$ are together joined to form a cyclic epoxide, whereby the
$R^9$ and $R^{10}$ substituents are on the same carbon or on adjacent carbon atoms;
$R^{11}$, which is bonded to substituent Z when Z is present or which is bonded directly to the camphor ring when Z is not present, is
(1) hydrogen,
(2) —$N(R^{12})$—CO—$R^{13}$ or
(3) —CO—$N(R^{14})$—$R^{15}$;
$R^{12}$ is
(1) hydrogen,
(2) alkoxy,
(3) unsubstituted or substituted alkyl where said substituent is one or more of carboxyl, hydroxyl, alkoxyl, alkoxycarbonyl, alkylsulfonyl or arylsulfonyl,
(4) alkoxycarbonyl,
(5) alkoxycarbonylamino or
(6) alkylsulfonylalkyl;
$R^{13}$ is
(1) hydrogen,
(2) alkoxyl,
(3) aralkoxyl,
(4) carboxyl,
(5) alkoxycarbonyl,
(6) alkoxycarbonylamino,
(7) unsubstituted or substituted cycloalkyl, wherein said substituent is carboxyl,
(8) unsubstituted or substituted phenyl wherein said substituent is one or more of carboxyl, carboxyalkyl or $SO_3H$,
(9) unsubstituted or substituted amino, wherein said substituent is unsubstituted or substituted alkyl where said substituent is one or more of carboxyl, alkylsulfonyl or unsubstituted 5-membered heterocyclic rings having 1 or 2 heteroatoms, where said heteroatom is N,
(10) unsubstituted or substituted heterocyclic rings selected from the group consisting of: pyrrolidinyl, imidazolyl, 1,2,4-triazolyl, tetrazolyl, tetrahydrofuranyl, furanyl, 1,3-dioxolanyl, thienyl, piperidinyl, piperazinyl, quinuclidinyl, morpholinyl, 1,3-tetrahydrothiazinyl, hexahydroazepinyl, tetrahydrothiopyranyl, 1-oxotetrahydrothiopyranyl and 1,1-dioxotetrahydrothiopyranyl wherein the linkage of the heterocyclic ring to the amidocarbonyl moiety can occur at a carbon atom or divalent nitrogen atom of the heterocyclic ring and wherein said substituent for any of said heterocyclic rings are one or more of alkyl, alkylcarbonyl, carboxyl, carboxyalkyl, carboxyaralkyl, aralkyl, aralkylcarbonyl, aralkoxy-carbonyl, alkoxycarbonyl, alkoxycarbonylalkyl, amino-alkylcarbonyl, cyano, alkylsulfonyl, alkoxycarbonyl-aminoalkylcarbonyl, oxo or unsubstituted or substituted amino wherein said substituent is one or more of alkyl, carboxylalkyl, alkoxycarbonyl or alkoxycarbonylalkyl or

(11) unsubstituted or substituted alkyl, wherein said substituent is one or more of hydroxyl, alkoxy, carboxyl, phenyl, hydroxyphenyl, alkylphenyl, carboxyalkylphenyl, cyano, alkylsulfonyl, acetamidino, formamidino, aminocarbonyl, alkylaminocarbonyl, aralkyl, aralkoxycarbonyl, halogen, thio, alkylthio, alkoxycarbonyl, alkoxycarbonylalkyl, Het, or unsubstituted or substituted amino, wherein said substituent is one or more of alkyl, deuterated alkyl, piperidinyl, Cyc, pyridinyl, morpholinyl, tetrahydropyranyl, tetrahydrothiapyranyl, tetrahydrothiapyranyl S-oxide, alkoxycarbonylpiperidinyl, cyano, cyanoalkyl, hydroxyalkyl, haloalkyl, dialkyl, alkylcarbonyl, carboxyl, alkylsulfonyl, carboxyalkyl, alkoxycarbonyl, alkoxycarbonylalkyl, aralkoxycarbonyl, aminoalkyl, aminocarbonyl, aminocarbonylalkyl, alkylaminocarbonyl, phenalkyl or unsubstituted or substituted alkylcarbonyl, where said substituent is a 5-membered heterocyclic ring having 1 or 2 heteroatoms and where said hetero atom is N, Cyc is defined as unsubstituted or substituted cycloalkyl wherein said substituent is alkoxycarbonyl, carboxyl, hydroxyl, oxo or spiro-dioxolanyl and Het is defined as unsubstituted or substituted heterocyclic rings selected from the group consisting of: pyrrolidinyl, imidazolyl, 1,2,4-triazolyl, tetrazolyl, tetrahydrofuranyl, furanyl, 1,3-dioxolanyl, thienyl, piperidinyl, piperazinyl, pyridinyl, quinuclidinyl, morpholinyl, 1,3-tetrahydrothiazinyl, hexahydroazepinyl, tetrahydropyranyl, tetrahydrothiopyranyl, 1-oxotetrahydrothiopyranyl and 1,1-dioxotetrahydrothiopyranyl wherein the linkage of the heterocyclic ring to the alkyl moiety can occur at a carbon atom or divalent nitrogen atom of the heterocyclic ring; and wherein said substituent for any of said heterocyclic rings are one or more of alkyl, amino, carboxyl, carboxyalkyl, aralkyl, carboxyaralkyl, alkoxycarbonyl, halogen substituted alkoxycarbonyl, alkoxycarbonylalkyl, alkoxyalkyl, alkoxyalkoxyalkyl, alkoxyalkoxyalkoxyalkyl, aralkylcarbonyl, aralkoxyalkyl, phenyl, aralkoxycarbonyl, oxo, SO$_3$H, or unsubstituted or substituted amino wherein said substituent is alkyl, carboxyl, carboxyalkyl, alkoxycarbonyl or alkoxycarbonylalkyl;

R$^{14}$ and R$^{15}$ are independently (1) hydrogen, (2) unsubstituted or substituted alkyl where said substituent is one or more of hydrogen, carboxyl, amino, aminoalkylamino, aminocarbonyl, hydroxyl, alkoxyl, alkylthio, thioalkyl, alkylsulfinyl, alkylsulfonyl, phenylalkoxycarbonyl, alkoxycarbonyl, indolyl, phenalkyl, hydroxyphenalkyl or unsubstituted 5-membered saturated heterocyclic rings having 1 or 2 hetero atoms wherein said hetero atom is N or (3) heterocyclic rings selected from the group consisting of: unsubstituted or substituted saturated or unsaturated rings having 5, 6, 7 or 8 total members and 1, 2, 3 or 4 N heteroatoms; having 5 or 6 total members and 1 or 2 O heteroatoms; having 5 or 6 total members and 1 S heteroatom; or having 6 total members and 2 different heteroatoms from the group consisting of N, O or S and wherein said substituent is one or more of alkyl, oxo, carboxyl, phenylalkyl, carboxyphenylalkyl or alkoxycarbonyl; and m and n are integers of from 0 to 1; and the pharmaceutically acceptable salts thereof.

In one embodiment is the method wherein the compound has the formula

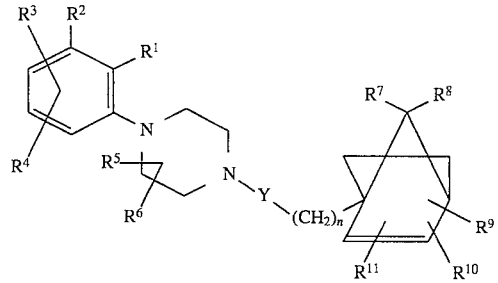

wherein
R$^{11}$ is (1) —N(R$^{12}$)—CO—R$^{13}$ or (2) —CO—N(R$^{14}$)—R$^{15}$; and R$^{13}$ is (1) hydrogen, (2) alkoxyl, (3) aralkoxyl, (4) carboxyl, (5) alkoxycarbonyl, (6) alkoxycarbonylamino, (7) unsubstituted or substituted cycloalkyl, wherein said substituent is carboxyl, (8) unsubstituted or substituted phenyl wherein said substituent is one or more of carboxyl, carboxyalkyl or SO$_3$H, (9) unsubstituted or substituted amino, wherein said substituent is unsubstituted or substituted alkyl where said substituent is one or more of carboxyl, alkylsulfonyl or unsubstituted 5-membered heterocyclic rings having 1 or 2 heteroatoms, where said heteroatom is N,

(10) unsubstituted or substituted heterocyclic rings selected from the group consisting of: pyrrolidinyl, imidazolyl, 1,2,4-triazolyl, tetrazolyl, tetrahydrofuranyl, furanyl, 1,3-dioxolanyl, thienyl, piperidinyl, piperazinyl, quinuclidinyl, morpholinyl, 1,3-tetrahydrothiazinyl, hexahydroazepinyl, tetrahydrothiopyranyl, 1-oxotetrahydrothiopyranyl and 1,1-dioxotetrahydrothiopyranyl wherein the linkage of the heterocyclic ring to the amidocarbonyl moiety can occur at a carbon atom or divalent nitrogen atom of the heterocyclic ring and wherein said substituent for any of said heterocyclic rings are one or more of alkyl, alkylcarbonyl, carboxyl, carboxyalkyl, carboxyaralkyl, aralkyl, aralkylcarbonyl, aralkoxy-carbonyl, alkoxycarbonyl, alkoxycarbonylalkyl, amino-alkylcarbonyl, cyano, alkylsulfonyl, alkoxycarbonyl-aminoalkylcarbonyl, oxo or unsubstituted or substituted amino wherein said substituent is one or more of alkyl, carboxyalkyl, alkoxycarbonyl or alkoxycarbonylalkyl or

(11) unsubstituted or substituted alkyl, wherein said substituent is one or more of hydroxyl, alkoxy, carboxyl, phenyl, hydroxyphenyl, alkylphenyl, carboxyalkylphenyl, cyano, alkylsulfonyl, acetamidino, formamidino, aminocarbonyl, alkylaminocarbonyl, aralkyl, aralkoxycarbonyl, halogen, thio, alkylthio, alkoxycarbonyl, alkoxycarbonylalkyl, Het, or unsubstituted or substituted amino, wherein said substituent is one or more of alkyl, deuterated alkyl, piperidinyl, Cyc, pyridinyl, morpholinyl, tetrahydropyranyl, tetrahydrothiapyranyl, tetrahydrothiapyranyl S-oxide, alkoxycarbonylpiperidinyl, cyano, cyanoalkyl, hydroxyalkyl, haloalkyl, dialkyl, alkylcarbonyl, carboxyl, alkylsulfonyl, carboxyalkyl, alkoxycarbonyl, alkoxycarbonylalkyl, aralkoxycarbonyl, aminoalkyl, aminocarbonyl, aminocarbonylalkyl, alkylaminocarbonyl, phenalkyl or unsubstituted or substituted alkylcarbonyl, where said substituent is a 5-membered heterocyclic ring having 1 heteroatom and where said heteroatom is N; Cyc is defined as unsubstituted or substituted cycloalkyl wherein said substituent is alkoxycarbonyl, carboxyl, hydroxyl, oxo or spiro-dioxolanyl and Het is defined as unsubstituted or substituted heterocyclic rings selected from the group consisting of: pyrrolidinyl, imidazolyl, 1,2,4-triazolyl, tetrazolyl, tetrahydrofuranyl, furanyl, 1,3-dioxolanyl, thienyl, piperidinyl, piperazinyl, pyridinyl, quinuclidinyl, morpholinyl, 1,3-tetrahydrothiazinyl, hexahydroazepinyl, tetrahydropyranyl, tetrahydrothio-pyranyl, 1-oxotetrahydrothiopyranyl and 1,1-dioxotetrahydrothiopyranyl wherein the linkage of the heterocyclic ring to the alkyl moiety can occur at a carbon atom or divalent nitrogen atom of the heterocyclic ring; and wherein said substituent for any of said heterocyclic rings are one or more of alkyl, amino, carboxyl, carboxyalkyl, aralkyl, carboxyaralkyl, alkoxycarbonyl, halogen substituted alkoxycarbonyl, alkoxycarbonylalkyl, alkoxyalkyl, alkoxyalkoxyalkyl, alkoxyalkoxyalkoxyalkyl, aralkylcarbonyl, aralkoxyalkyl, phenyl, aralkoxycarbonyl, oxo, SO$_3$H, or unsubstituted or substituted amino wherein said substituent is alkyl, carboxyl, carboxyalkyl, alkoxycarbonyl or alkoxycarbonylalkyl.

In a class is the method wherein the compound has the formula

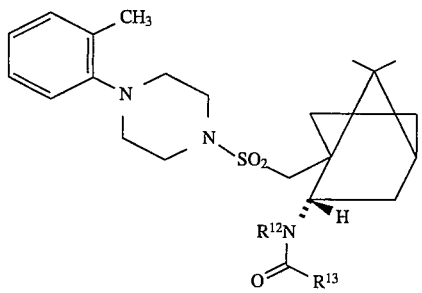

wherein
R$^{12}$ is
(1) hydrogen,
(2) alkoxycarbonyl or
(3) unsubstituted of substituted alkyl wherein said substituent is hydroxyl, alkoxyl, carboxyl, carboxyalky, alkylsulfonyl or alkoxycarbonyl;

R$^{13}$ is
(1) hydrogen,
(2) alkoxyl,
(3) aralkoxyl,
(4) alkoxycarbonyl,
(5) alkoxycarbonylamino,
(6) unsubstituted or substituted cycloalkyl, wherein said substituent is carboxyl,
(7) unsubstituted or substituted phenyl wherein said substituent is one or more of carboxyl, carboxyalkyl or SO$_3$H,
(8) unsubstituted or substituted amino, wherein said substituent is unsubstituted or substituted alkyl where said substituent is one or more of carboxyl, alkylsulfonyl or unsubstituted 5-membered heterocyclic rings having 1 or 2 heteroatoms, where said heteroatom is N,
(9) unsubstituted or substituted heterocyclic rings of the Formulae

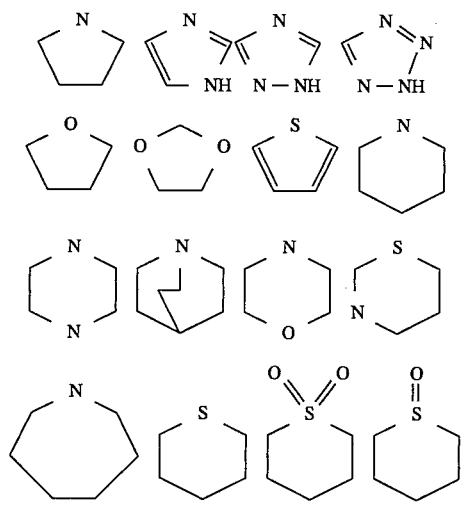

wherein the linkage of the heterocyclic ring to the amidocarbonyl moiety can occur at a carbon atom or divalent nitrogen atom of the heterocyclic ring and where said substituents on said heterocyclic ring are one or more of alkyl, carboxyl, carboxyalkyl, carboxyaralkyl, aralkylcarbonyl, aralkoxy-carbonyl, alkoxycarbonyl, alkoxycarbonylalkyl, alkoxy-carbonylaminoalkylcarbonyl, oxo or unsubstituted or substituted amino wherein said substituent is one or more of alkyl, carboxylalkyl, alkoxycarbonyl or alkoxycarbonylalkyl or

(10) unsubstituted or substituted alkyl, wherein said substituent is one or more of hydroxyl, carboxyl, carboxyalkylphenyl, alkylsulfonyl, aminocarbonyl, alkylaminocarbonyl, aralkyl, aralkoxycarbonyl, halogen, alkoxycarbonyl, alkoxycarbonylalkyl, Het or unsubstituted or substituted amino, wherein said substituent is one or more of alkyl, deuterated alkyl, cyanoalkyl, hydroxyalkyl, haloalkyl, dialkyl, alkylcarbonyl, alkylsulfonyl, carboxyalkyl, aminoalkyl, Cyc, piperidinyl, alkoxycarbonylpiperidinyl, pyridinyl, tetrahydropyranyl, tetrahydrothiopyranyl, tetrahydrothiopyranyl S-oxide, alkoxycarbonyl, alkoxycarbonylalkyl, aralkoxycarbonyl, aminocarbonylalkyl, alkylaminocarbonyl, phenalkyl or unsubstituted or substituted alkylcarbonyl, where said substituent is a 5-membered heterocyclic ring having 1 heteroatom and where said hetero atom is N, where Cyc is defined as substituted or unsubstituted cycloalkyl wherein said substituent is alkoxycarbonyl, carboxyl, hydroxyl, oxo or spiro-dioxolanyl and Het is defined as unsubstituted or substituted heterocyclic rings of the Formulae

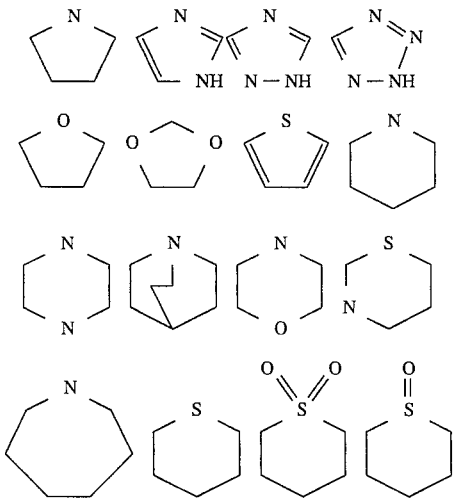

wherein the linkage of the heterocyclic ring to the alkyl moiety can occur at a carbon atom or divalent nitrogen atom of the heterocyclic ring and where said substituent on said heterocyclic ring is one or more of alkyl, amino, carboxyl, carboxyalkyl, carboxyaralkyl, alkoxycarbonyl, halogen substituted alkoxycarbonyl, alkoxycarbonylalkyl, alkoxyalkoxyalkyl, alkoxyalkoxyalkoxyalkyl, aralkylcarbonyl, aralkoxyalkyl, aralkoxyalkyl, aralkoxycarbonyl, oxo, $SO_3H$, or unsubstituted or substituted amino wherein said substituent is alkyl, carboxyalkyl, alkoxycarbonyl or alkoxycarbonylalkyl.

In a subclass is the method wherein
$R^{12}$ is
(1) hydrogen, or
(2) unsubstituted alkyl; and
$R^{13}$ is
(1) aralkoxyl,
(2) unsubstituted or substituted heterocyclic rings of the Formulae

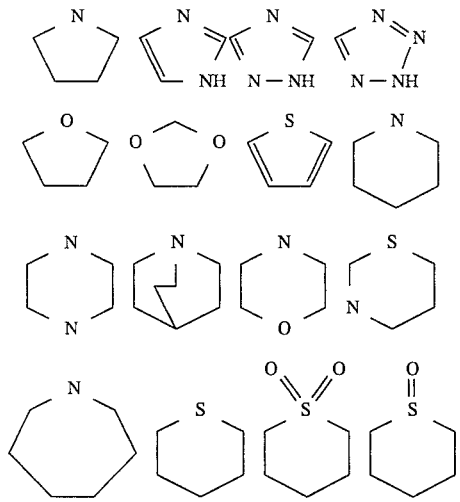

wherein the linkage of the heterocyclic ring to the amidocarbonyl moiety can occur at a carbon atom or divalent nitrogen atom of the heterocyclic ring and where said substituents on said heterocyclic ring are one or more of alkyl, carboxyl, carboxyalkyl, carboxyaralkyl, aralkylcarbonyl, aralkoxy-carbonyl, alkoxycarbonyl, alkoxycarbonylalkyl, alkoxy-carbonylaminoalkylcarbonyl, oxo or unsubstituted or substituted amino wherein said substituent is one or more of alkyl, carboxylalkyl, alkoxycarbonyl or alkoxycarbonylalkyl or (3) unsubstituted or substituted alkyl, wherein said substituent is one or more of hydroxyl, alkylsulfonyl, Het or unsubstituted or substituted amino, wherein said substituent is one or more of alkyl, deuterated alkyl, cyanoalkyl, hydroxyalkyl, haloalkyl, dialkyl, alkylcarbonyl, alkylsulfonyl, carboxyalkyl, aminoalkyl, Cyc, piperidinyl, alkoxycarbonylpiperidinyl, pyridinyl, tetrahydropyranyl, tetrahydrothiopyranyl, tetrahydrothiopyranyl S-oxide, alkoxycarbonyl or alkoxycarbonylalkyl; where Cyc is defined as substituted or unsubstituted cycloalkyl wherein said substituent is alkoxycarbonyl, carboxyl, and Het is defined as unsubstituted or substituted heterocyclic rings of the Formulae

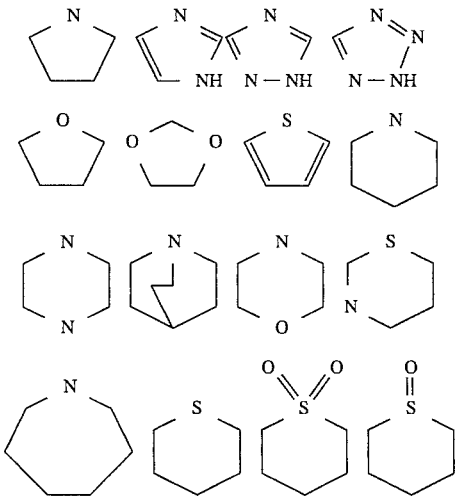

wherein the linkage of the heterocyclic ring to the alkyl moiety can occur at a carbon atom or divalent nitrogen atom of the heterocyclic ring and where said substituent on said heterocyclic ring is one or more of alkyl, amino, carboxyl, carboxyalkyl, carboxyaralkyl, alkoxycarbonyl, halogen substituted alkoxycarbonyl, alkoxycarbonylalkyl, alkoxyalkoxyalkyl, alkoxyalkoxyalkoxyalkyl, aralkylcarbonyl, aralkoxyalkyl, aralkoxyalkyl, aralkoxycarbonyl, oxo, $SO_3H$, or unsubstituted or substituted amino wherein said substituent is alkyl, carboxyalkyl, alkoxycarbonyl or alkoxycarbonylalkyl.

Illustrative of the invention is the method wherein the compound is

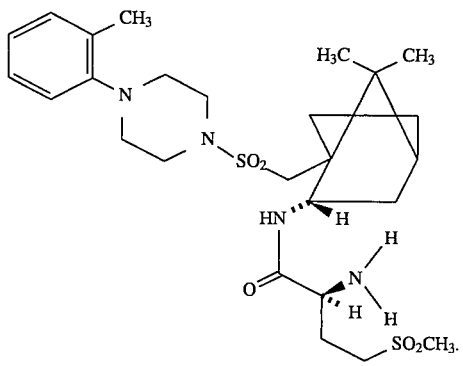

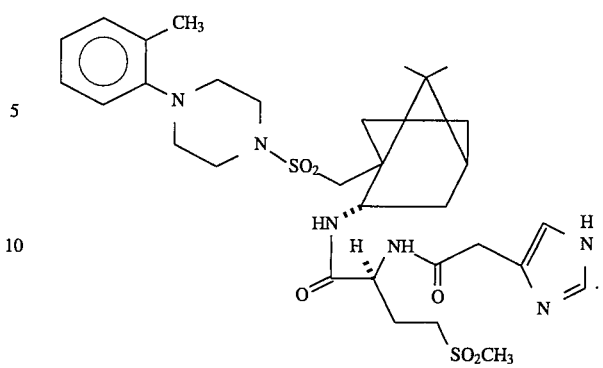

An illustration of the invention is the method wherein the compound is administered at a daily dosage of 1 to 100 mg/kg, preferably 1 to 20 mg/kg.

More particularly illustrating the present invention is the method wherein the compound is administered orally, subcutaneously or intravenously. Exemplifying the invention is the method wherein the compound is administered orally.

An example of the present invention is the method wherein the compound is administered on between day 10 and day 15 of the estrous cycle after fertilization of the farm animal, preferably on between day 12 and day 15 of the estrous cycle after fertilization. Further illustrating the invention is the method wherein the compound is administered on between day 10 and day 15 of the estrous cycle for a period of one day to three weeks, preferably one week to three weeks, most preferably, one week to two weeks. More specifically exemplifying the invention is the method wherein the compound is administered on between day 10 and day 15 of the estrous cycle for a period of one day to three weeks at a daily dosage of 1 to 100 mg/kg, preferably 1 to 20 mg/kg. Further exemplifying the invention is the method wherein the compound is administered orally on between day 10 and day 15 of the estrous cycle and continuing for a period of one day to three weeks at a daily dosage of 1 to 100 mg/kg.

Another example of the invention is the method wherein the increased fertility is accomplished by prolonging corpus luteal function for egg implantation. More specifically illustrating the invention is the method wherein prolongation of corpus luteal function results in reduction of embryonic loss.

Another illustration of the invention is the method wherein Compound A is administered on between day 10 and day 15 of the estrous cycle after fertilization for a period of one day to three weeks at a daily dosage of 1 to 100 mg/kg. More particularly exemplifying the invention is the method wherein Compound A is administered orally.

Further illustrating the invention is the method of increasing fertility and embryonic survival in a farm animal wherein the compound is Also included in the present invention is a method for improving survival of a farm animal neonate comprising controlling timing of parturition to effect delivery of the neonate during daylight hours by administering to a farm animal which is expected to deliver the neonate within 24 hours a pharmacologically effective amount of a compound of the formula I

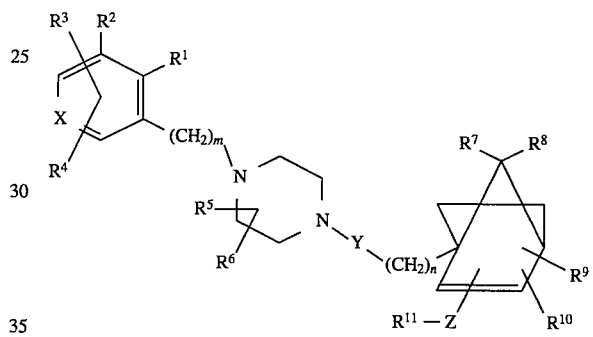

wherein
X is
(1) C or
(2) N;
Y is (1) carbonyl or
(2) sulfonyl;
Z is an optional substituent that, when present, is substituted or unsubstituted alkyl where said substituent is carboxyl;
$R^1$ is
(1) hydrogen,
(2) alkyl or
(3) $NH_2$;
$R^2$ is
(1) hydrogen, or
$R^1$ and $R^2$ together are bridged alkyl of three or four methylenes so as to form either

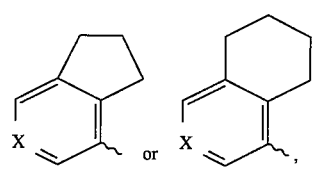

respectively;
$R^3$ and $R^4$ are independently one or more of
(1) hydrogen,
(2) halogen, (3) alkylsulfonyl, (4) alkoxy or (5) unsubstituted or substituted alkyl wherein said substituent is hydroxyl, alkoxyl, alkylsulfonyl, amino, alkylamino or dialkylamino;

$R^5$ and $R^6$ are independently selected from (1) hydrogen, (2) alkyl, (3) substituted alkyl where said substituent is amino, hydroxyl, alkoxyl, alkylsulfonyl, arylsulfonyl, alkylamino or dialkylamino, (4) phenylalkyl or (5) oxo;

$R^7$ and $R^8$ are independently one or more of (1) hydrogen, (2) alkyl or (3) joined together to form unsubstituted or substituted cycloalkyl where said substituent is hydroxy or hydroxyalkyl;

$R^9$ and $R^{10}$ are independently selected from (1) hydrogen, (2) hydroxyl, (3) halogen, (4) oximino, (5) methyl, (6) carboxyl, (7) oxo, (8) alkoxycarbonyl, (9) alkylcarbonyloxy,

(10) alkoxycarbonylalkoxy,

(11) sulfonyloxy,

(12) trihaloalkylsulfonyloxo or

(13) unsubstituted or substituted amino where said substituent is one or more of alkyl, carboxyalkyl or alkoxycarbonylalkyl; or $R^9$ and $R^{10}$ are together joined to form a cyclic epoxide, whereby the $R^9$ and $R^{10}$ substituents are on the same carbon or on adjacent carbon atoms;

$R^{11}$, which is bonded to substituent Z when Z is present or which is bonded directly to the camphor ring when Z is not present, is (1) hydrogen, (2) —N($R^{12}$)—CO—$R^{13}$ or (3) —CO—N($R^{14}$)—$R^{15}$;

$R^{12}$ is (1) hydrogen, (2) alkoxy, (3) unsubstituted or substituted alkyl where said substituent is one or more of carboxyl, hydroxyl, alkoxyl, alkoxycarbonyl, alkylsulfonyl or arylsulfonyl, (4) alkoxycarbonyl, (5) alkoxycarbonylamino or (6) alkylsulfonylalkyl;

$R^{13}$ is (1) hydrogen, (2) alkoxyl, (3) aralkoxyl, (4) carboxyl, (5) alkoxycarbonyl, (6) alkoxycarbonylamino,.

(7) unsubstituted or substituted cycloalkyl, wherein said substituent is carboxyl, (8) unsubstituted or substituted phenyl wherein said substituent is one or more of carboxyl, carboxyalkyl or $SO_3H$, (9) unsubstituted or substituted amino, wherein said substituent is unsubstituted or substituted alkyl where said substituent is one or more of carboxyl, alkylsulfonyl or unsubstituted 5-membered heterocyclic rings having 1 or 2 heteroatoms, where said heteroatom is N,

(10) unsubstituted or substituted heterocyclic rings selected from the group consisting of: pyrrolidinyl, imidazolyl, 1,2,4-triazolyl, tetrazolyl, tetrahydrofuranyl, furanyl, 1,3-dioxolanyl, thienyl, piperidinyl, piperazinyl, quinuclidinyl, morpholinyl, 1,3-tetrahydrothiazinyl, hexahydroazepinyl, tetrahydrothiopyranyl, 1-oxotetrahydrothiopyranyl and 1,1-dioxotetrahydrothiopyranyl wherein the linkage of the heterocyclic ring to the amidocarbonyl moiety can occur at a carbon atom or divalent nitrogen atom of the heterocyclic ring and wherein said substituent for any of said heterocyclic rings are one or more of alkyl, alkylcarbonyl, carboxyl, carboxyalkyl, carboxyaralkyl, aralkyl, aralkylcarbonyl, aralkoxy-carbonyl, alkoxycarbonyl, alkoxycarbonylalkyl, amino-alkylcarbonyl, cyano, alkylsulfonyl, alkoxycarbonyl-aminoalkylcarbonyl, oxo or unsubstituted or substituted amino wherein said substituent is one or more of alkyl, carboxylalkyl, alkoxycarbonyl or alkoxycarbonylalkyl or

(11) unsubstituted or substituted alkyl, wherein said substituent is one or more of hydroxyl, alkoxy, carboxyl, phenyl, hydroxyphenyl, alkylphenyl, carboxyalkylphenyl, cyano, alkylsulfonyl, acetamidino, formamidino, aminocarbonyl, alkylaminocarbonyl, aralkyl, aralkoxycarbonyl, halogen, thio, alkylthio, alkoxycarbonyl, alkoxycarbonylalkyl, Het, or unsubstituted or substituted amino, wherein said substituent is one or more of alkyl, deuterated alkyl, piperidinyl, Cyc, pyridinyl, morpholinyl, tetrahydropyranyl, tetrahydrothiapyranyl, tetrahydrothiapyranyl S-oxide, alkoxycarbonylpiperidinyl, cyano, cyanoalkyl, hydroxyalkyl, haloalkyl, dialkyl, alkylcarbonyl, carboxyl, alkylsulfonyl, carboxyalkyl, alkoxycarbonyl, alkoxycarbonylalkyl, aralkoxycarbonyl, aminoalkyl, aminocarbonyl, aminocarbonylalkyl, alkylaminocarbonyl, phenalkyl or unsubstituted or substituted alkylcarbonyl, where said substituent is a 5-membered heterocyclic ring having 1 or 2 heteroatoms and where said hetero atom is N, Cyc is defined as unsubstituted or substituted cycloalkyl wherein said substituent is alkoxycarbonyl, carboxyl, hydroxyl, oxo or spiro-dioxolanyl and Het is defined as unsubstituted or substituted heterocyclic rings selected from the group consisting of: pyrrolidinyl, imidazolyl, 1,2,4-triazolyl, tetrazolyl, tetrahydrofuranyl, furanyl, 1,3-dioxolanyl, thienyl, piperidinyl, piperazinyl, pyridinyl, quinuclidinyl, morpholinyl, 1,3-tetrahydrothiazinyl, hexahydroazepinyl, tetrahydropyranyl, tetrahydrothiopyranyl, 1-oxotetrahydrothiopyranyl and 1,1-dioxotetrahydrothiopyranyl wherein the linkage of the heterocyclic ring to the alkyl moiety can occur at a carbon atom or divalent nitrogen atom of the heterocyclic ring; and wherein said substituent for any of said heterocyclic rings are one or more of alkyl, amino, carboxyl, carboxyalkyl, aralkyl, carboxyaralkyl, alkoxycarbonyl, halogen substituted alkoxycarbonyl, alkoxycarbonylalkyl, alkoxyalkyl, alkoxyalkoxyalkyl, alkoxyalkoxyalkoxyalkyl, aralkylcarbonyl, aralkoxyalkyl, phenyl, aralkoxycarbonyl, oxo, SO₃H, or unsubstituted or substituted amino wherein said substituent is alkyl, carboxyl, carboxyalkyl, alkoxycarbonyl or alkoxycarbonylalkyl;

$R^{14}$ and $R^{15}$ are independently (1) hydrogen, (2) unsubstituted or substituted alkyl where said substituent is one or more of hydrogen, carboxyl, amino, aminoalkylamino, aminocarbonyl, hydroxyl, alkoxyl, alkylthio, thioalkyl, alkylsulfinyl, alkylsulfonyl, phenylalkoxycarbonyl, alkoxycarbonyl, indolyl, phenalkyl, hydroxyphenalkyl or unsubstituted 5-membered saturated heterocyclic rings having 1 or 2 hetero atoms wherein said hetero atom is N or (3) heterocyclic rings selected from the group consisting of: unsubstituted or substituted saturated or unsaturated rings having 5, 6, 7 or 8 total members and 1, 2, 3 or 4 N heteroatoms; having 5 or 6 total members and 1 or 2 O heteroatoms; having 5 or 6 total members and 1 S heteroatom; or having 6 total members and 2 different heteroatoms from the group consisting of N, O or S and wherein said substituent is one or more of alkyl, oxo, carboxyl, phenylalkyl, carboxyphenylalkyl or alkoxycarbonyl; and m and n are integers of from 0 to 1; and the pharmaceutically acceptable salts thereof.

In one embodiment is the method for improving survival of a farm animal neonate wherein the compound has the formula

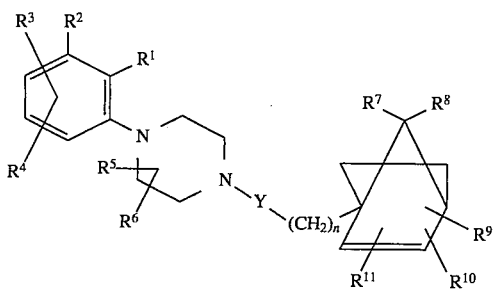

wherein $R^{11}$ is (1) —N($R^{12}$)—CO—$R^{13}$ or (2) —CO—N($R^{14}$)—$R^{15}$; and $R^{13}$ is (1) hydrogen, (2) alkoxyl, (3) aralkoxyl, (4) carboxyl, (5) alkoxycarbonyl, (6) alkoxycarbonylamino, (7) unsubstituted or substituted cycloalkyl, wherein said substituent is carboxyl, (8) unsubstituted or substituted phenyl wherein said substituent is one or more of carboxyl, carboxyalkyl or SO₃H, (9) unsubstituted or substituted amino, wherein said substituent is unsubstituted or substituted alkyl where said substituent is one or more of carboxyl, alkylsulfonyl or unsubstituted 5-membered heterocyclic rings having 1 or 2 heteroatoms, where said heteroatom is N,

(10) unsubstituted or substituted heterocyclic rings selected from the group consisting of: pyrrolidinyl, imidazolyl, 1,2,4-triazolyl, tetrazolyl, tetrahydrofuranyl, furanyl, 1,3-dioxolanyl, thienyl, piperidinyl, piperazinyl, quinuclidinyl, morpholinyl, 1,3-tetrahydrothiazinyl, hexahydroazepinyl, tetrahydrothiopyranyl, 1-oxotetrahydrothiopyranyl and 1,1-dioxotetrahydrothiopyranyl wherein the linkage of the heterocyclic ring to the amidocarbonyl moiety can occur at a carbon atom or divalent nitrogen atom of the heterocyclic ring and wherein said substituent for any of said heterocyclic rings are one or more of alkyl, alkylcarbonyl, carboxyl, carboxyalkyl, carboxyaralkyl, aralkyl, aralkylcarbonyl, aralkoxycarbonyl, alkoxycarbonyl, alkoxycarbonylalkyl, aminoalkylcarbonyl, cyano, alkylsulfonyl, alkoxycarbonylaminoalkylcarbonyl, oxo or unsubstituted or substituted amino wherein said substituent is one or more of alkyl, carboxyalkyl, alkoxycarbonyl or alkoxycarbonylalkyl or

(11) unsubstituted or substituted alkyl, wherein said substituent is one or more of hydroxyl, alkoxy, carboxyl, phenyl, hydroxyphenyl, alkylphenyl, carboxyalkylphenyl, cyano, alkylsulfonyl, acetamidino, formamidino, aminocarbonyl, alkylaminocarbonyl, aralkyl, aralkoxycarbonyl, halogen, thio, alkylthio, alkoxycarbonyl, alkoxycarbonylalkyl, Het, or unsubstituted or substituted amino, wherein said substituent is one or more of alkyl, deuterated alkyl, piperidinyl, Cyc, pyridinyl, morpholinyl, tetrahydropyranyl, tetrahydrothiapyranyl, tetrahydrothiapyranyl S-oxide, alkoxycarbonylpiperidinyl, cyano, cyanoalkyl, hydroxyalkyl, haloalkyl, dialkyl, alkylcarbonyl, carboxyl, alkylsulfonyl, carboxyalkyl, alkoxycarbonyl, alkoxycarbonylalkyl, aralkoxycarbonyl, aminoalkyl, aminocarbonyl, aminocarbonylalkyl, alkylaminocarbonyl, phenalkyl or unsubstituted or substituted alkylcarbonyl, where said substituent is a 5-membered heterocyclic ring having 1 heteroatom and where said heteroatom is N, Cyc is defined as unsubstituted or substituted cycloalkyl wherein said substituent is alkoxycarbonyl, carboxyl, hydroxyl, oxo or spiro-dioxolanyl and Het is defined as unsubstituted or substituted heterocyclic rings selected from the group consisting of: pyrrolidinyl, imidazolyl, 1,2,4-triazolyl, tetrazolyl, tetrahydrofuranyl, furanyl, 1,3-dioxolanyl, thienyl, piperidinyl, piperazinyl, pyridinyl, quinuclidinyl, morpholinyl, 1,3-tetrahydrothiazinyl, hexahydroazepinyl, tetrahydropyranyl, tetrahydrothiopyranyl, 1-oxotetrahydrothiopyranyl and 1,1-dioxotetrahydrothiopyranyl wherein the linkage of the heterocyclic ring to the alkyl moiety can occur at a carbon atom or divalent nitrogen atom of the heterocyclic ring; and wherein said substituent for any of said heterocyclic rings are one or more of alkyl, amino, carboxyl, carboxyalkyl, aralkyl, carboxyaralkyl, alkoxycarbonyl, halogen substituted alkoxycarbonyl, alkoxycarbonylalkyl, alkoxyalkyl, alkoxyalkoxyalkyl, alkoxyalkoxyalkoxyalkyl, aralkylcarbonyl, aralkoxyalkyl, phenyl, aralkoxycarbonyl, oxo, SO₃H, or unsubstituted or substituted amino wherein said substituent is alkyl, carboxyl, carboxyalkyl, alkoxycarbonyl or alkoxycarbonylalkyl.

In a class is the method for improving survival of a farm animal neonate, further comprising monitoring the neonate after delivery during the daylight hours.

In a subclass is the method for improving survival of a farm animal neonate, wherein the compound has the formula

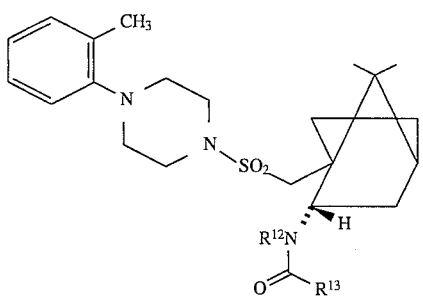

wherein
R$^{12}$ is
(1) hydrogen,
(2) alkoxycarbonyl or
(3) unsubstituted of substituted alkyl wherein said substituent is hydroxyl, alkoxyl, carboxyl, carboxyalky, alkylsulfonyl or alkoxycarbonyl;
R$^{13}$ is
(1) hydrogen,
(2) alkoxyl,
(3) aralkoxyl,
(4) alkoxycarbonyl,
(5) alkoxycarbonylamino,
(6) unsubstituted or substituted cycloalkyl, wherein said substituent is carboxyl,
(7) unsubstituted or substituted phenyl wherein said substituent is one or more of carboxyl, carboxyalkyl or SO$_3$H,
(8) unsubstituted or substituted amino, wherein said substituent is unsubstituted or substituted alkyl where said substituent is one or more of carboxyl, alkylsulfonyl or unsubstituted 5-membered heterocyclic rings having 1 or 2 heteroatoms, where said heteroatom is N,
(9) unsubstituted or substituted heterocyclic rings of the Formulae

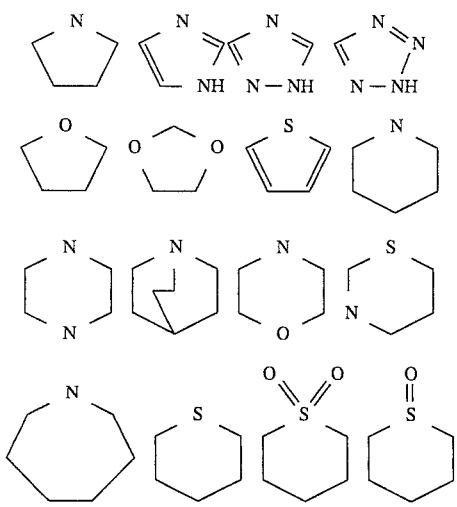

wherein the linkage of the heterocyclic ring to the amidocarbonyl moiety can occur at a carbon atom or divalent nitrogen atom of the heterocyclic ring and where said substituents on said heterocyclic ring are one or more of alkyl, carboxyl, carboxyalkyl, carboxyaralkyl, aralkylcarbonyl, aralkoxycarbonyl, alkoxycarbonyl, alkoxycarbonylalkyl, alkoxycarbonylaminoalkylcarbonyl, oxo or unsubstituted or substituted amino wherein said substituent is one or more of alkyl, carboxylalkyl, alkoxycarbonyl or alkoxycarbonylalkyl or

(10) unsubstituted or substituted alkyl, wherein said substituent is one or more of hydroxyl, carboxyl, carboxyalkylphenyl, alkylsulfonyl, aminocarbonyl, alkylaminocarbonyl, aralkyl, aralkoxycarbonyl, halogen, alkoxycarbonyl, alkoxycarbonylalkyl, Het or unsubstituted or substituted amino, wherein said substituent is one or more of alkyl, deuterated alkyl, cyanoalkyl, hydroxyalkyl, haloalkyl, dialkyl, alkylcarbonyl, alkylsulfonyl, carboxyalkyl, aminoalkyl, Cyc, piperidinyl, alkoxycarbonylpiperidinyl, pyridinyl, tetrahydropyranyl, tetrahydrothiopyranyl, tetrahydrothiopyranyl S-oxide, alkoxycarbonyl, alkoxycarbonylalkyl, aralkoxycarbonyl, aminocarbonylalkyl, alkylaminocarbonyl, phenalkyl or unsubstituted or substituted alkylcarbonyl, where said substituent is a 5-membered heterocyclic ring having 1 heteroatom and where said hetero atom is N, where Cyc is defined as substituted or unsubstituted cycloalkyl wherein said substituent is alkoxycarbonyl, carboxyl, hydroxyl, oxo or spiro-dioxolanyl and Het is defined as unsubstituted or substituted heterocyclic rings of the Formulae

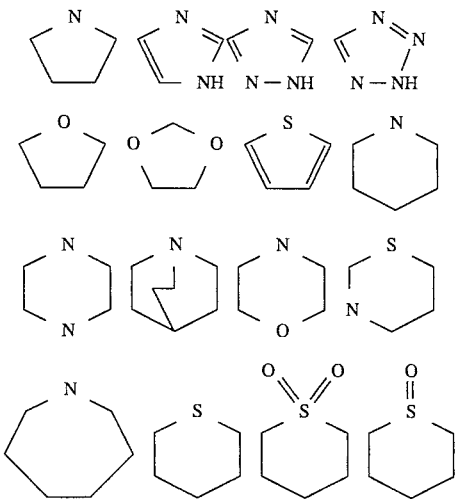

wherein the linkage of the heterocyclic ring to the alkyl moiety can occur at a carbon atom or divalent nitrogen atom of the heterocyclic ring and where said substituent on said heterocyclic ring is one or more of alkyl, amino, carboxyl, carboxyalkyl, carboxyaralkyl, alkoxycarbonyl, halogen substituted alkoxycarbonyl, alkoxycarbonylalkyl, alkoxyalkoxyalkyl, alkoxyalkoxyalkoxyalkyl, aralkylcarbonyl, aralkoxyalkyl, aralkoxyalkyl, aralkoxycarbonyl, oxo, SO$_3$H, or unsubstituted or substituted amino wherein said substituent is alkyl, carboxyalkyl, alkoxycarbonyl or alkoxycarbonylalkyl.

Illustrative of the invention the method for improving survival of a farm animal neonate wherein
R$^{12}$ is
(1) hydrogen, or
(2) unsubstituted alkyl; and
R$^{13}$ is
(1) aralkoxyl,
(2) unsubstituted or substituted heterocyclic rings of the Formulae

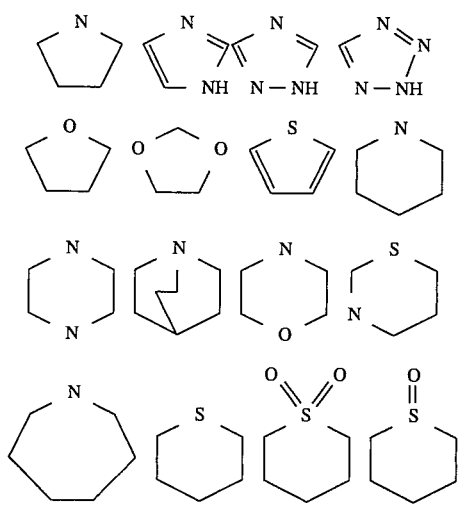

wherein the linkage of the heterocyclic ring to the amidocarbonyl moiety can occur at a carbon atom or divalent nitrogen atom of the heterocyclic ring and where said substituents on said heterocyclic ring are one or more of alkyl, carboxyl, carboxyalkyl, carboxyaralkyl, aralkylcarbonyl, aralkoxycarbonyl, alkoxycarbonyl, alkoxycarbonylalkyl, alkoxycarbonylaminoalkylcarbonyl, oxo or unsubstituted or substituted amino wherein said substituent is one or more of alkyl, carboxylalkyl, alkoxycarbonyl or alkoxycarbonylalkyl or (3) unsubstituted or substituted alkyl, wherein said substituent is one or more of hydroxyl, alkylsulfonyl, Het or unsubstituted or substituted amino, wherein said substituent is one or more of alkyl, deuterated alkyl, cyanoalkyl, hydroxyalkyl, haloalkyl, dialkyl, alkylcarbonyl, alkylsulfonyl, carboxyalkyl, aminoalkyl, Cyc, piperidinyl, alkoxycarbonylpiperidinyl, pyridinyl, tetrahydropyranyl, tetrahydrothiopyranyl, tetrahydrothiopyranyl S-oxide, alkoxycarbonyl or alkoxycarbonylalkyl; where Cyc is defined as substituted or unsubstituted cycloalkyl wherein said substituent is alkoxycarbonyl, carboxyl, and Het is defined as unsubstituted or substituted heterocyclic rings of the Formulae

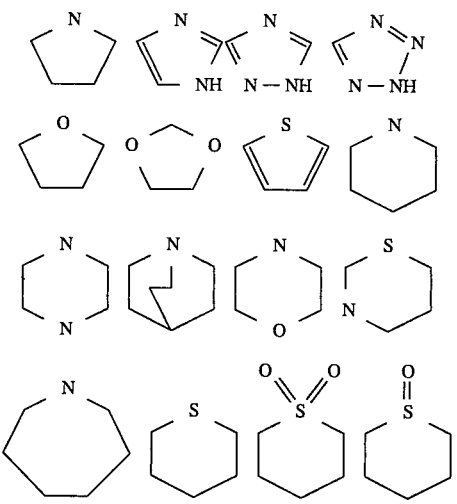

wherein the linkage of the heterocyclic ring to the alkyl moiety can occur at a carbon atom or divalent nitrogen atom of the heterocyclic ring and where said substituent on said heterocyclic ring is one or more of alkyl, amino, carboxyl, carboxyalkyl, carboxyaralkyl, alkoxycarbonyl, halogen substituted alkoxycarbonyl, alkoxycarbonylalkyl, alkoxyalkoxyalkyl, alkoxyalkoxyalkoxyalkyl, aralkylcarbonyl, aralkoxyalkyl, aralkoxyalkyl, aralkoxycarbonyl, oxo, SO₃H, or unsubstituted or substituted amino wherein said substituent is alkyl, carboxyalkyl, alkoxycarbonyl or alkoxycarbonylalkyl.

Exemplifying the invention is the method for improving survival of a farm animal neonate, wherein the compound is

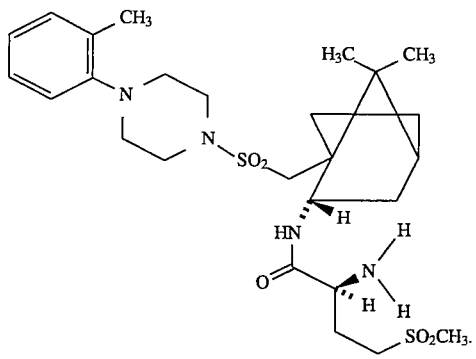

An illustration of the invention is the method for improving survival of a farm animal neonate, wherein the compound is administered at a daily dosage of 1 to 100 mg/kg, preferably 1 to 20 mg/kg. Further exemplify the invention is the method for improving survival of a farm animal neonate, wherein the compound is administered orally to the farm animal at a daily dosage of 1 to 100 mg/kg on the evening before delivery is expected.

An example of the invention is the method for improving survival of a farm animal neonate, wherein Compound A is administered at a daily dosage of I to 100 mg/kg. More particularly illustrating the invention is the method for improving survival of a farm animal neonate, wherein Compound A is administered orally to the farm animal at a daily dosage of I to 100 mg/kg on the evening before delivery is expected.

Further exemplifying the invention is the method for improving survival of a farm animal neonate, wherein the compound is

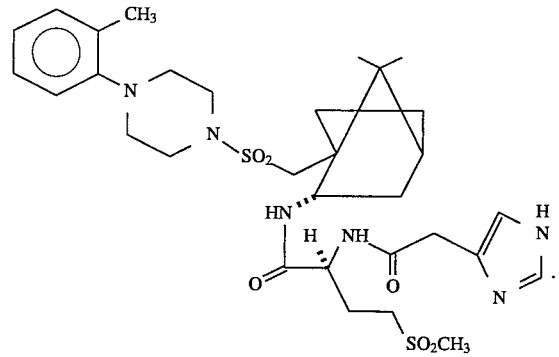

Also included in the instant invention is a method of controlling the timing of estrus in a farm animal, comprising administering to the farm animal a pharmacologically effective amount of a compound of formula I

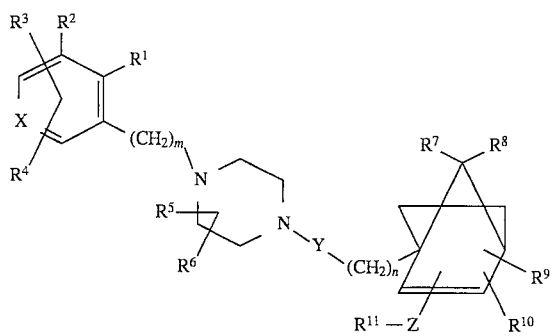

wherein
X is
(1) C or
(2) N;
Y is
(1) carbonyl or
(2) sulfonyl;
Z is an optional substituent that, when present, is substituted or unsubstituted alkyl where said substituent is carboxyl;
$R^1$ is
(1) hydrogen,
(2) alkyl or
(3) $NH_2$;
$R^2$ is hydrogen, or
$R^1$ and $R^2$ together are bridged alkyl of three or four methylenes;
$R^3$ and $R^4$ are independently one or more of
(1) hydrogen,
(2) halogen,
(3) alkylsulfonyl,
(4) alkoxy or
(5) unsubstituted or substituted alkyl wherein said substituent is hydroxyl, alkoxyl, alkylsulfonyl, amino, alkylamino or dialkylamino;
$R^5$ and $R^6$ are independently selected from
(1) hydrogen,
(2) alkyl,
(3) substituted alkyl where said substituent is amino, hydroxyl, alkoxyl, alkylsulfonyl, arylsulfonyl, alkylamino or dialkylamino,
(4) phenylalkyl or
(5) oxo;
$R^7$ and $R^8$ are independently one or more of
(1) hydrogen,
(2) alkyl or
(3) joined together to form unsubstituted or substituted cycloalkyl where said substituent is hydroxy or hydroxyalkyl;
$R^9$ and $R^{10}$ are independently selected from
(1) hydrogen,
(2) hydroxyl,
(3) halogen,
(4) oximino,
(5) methyl,
(6) carboxyl,
(7) oxo,
(8) alkoxycarbonyl,
(9) alkylcarbonyloxy,
(10) alkoxycarbonylalkoxy,
(11) sulfonyloxy,
(12) trihaloalkylsulfonyloxo or
(13) unsubstituted or substituted amino where said substituent is one or more of alkyl, carboxyalkyl or alkoxycarbonylalkyl; or
$R^9$ and $R^{10}$ are together joined to form a cyclic epoxide, whereby the $R^9$ and $R^{10}$ substituents are on the same carbon or on adjacent carbon atoms;
$R^{11}$ is
(1) hydrogen,
(2) $-N(R^{12})-CO-R^{13}$ or
(13) $-CO-N(R^{14})-R^{15}$;
$R^{12}$ is
(1) hydrogen,
(2) alkoxy,
(3) unsubstituted or substituted alkyl where said substituent is one or more of carboxyl, hydroxyl, alkoxyl, alkoxycarbonyl, alkylsulfonyl or arylsulfonyl,
(4) alkoxycarbonyl,
(5) alkoxycarbonylamino or
(6) alkylsulfonylalkyl;
$R^{13}$ is
(1) hydrogen,
(2) alkoxyl,
(3) aralkoxyl,
(4) carboxyl,
(5) alkoxycarbonyl,
(6) alkoxycarbonylamino,
(7) unsubstituted or substituted cycloalkyl, wherein said substituent is carboxyl,
(8) unsubstituted or substituted phenyl wherein said substituent is one or more of carboxyl, carboxyalkyl or $SO_3H$,
(9) unsubstituted or substituted amino, wherein said substituent is unsubstituted or substituted alkyl where said substituent is one or more of carboxyl, alkylsulfonyl or unsubstituted 5-membered heterocyclic rings having 1 or 2 heteroatoms, where said heteroatom is N,
(10) unsubstituted or substituted heterocyclic rings selected from the group consisting of: pyrrolidinyl, imidazolyl, 1,2,4-triazolyl, tetrazolyl, tetrahydrofuranyl, furanyl, 1,3-dioxolanyl, thienyl, piperidinyl, piperazinyl, quinuclidinyl, morpholinyl, 1,3-tetrahydrothiazinyl, hexahydroazepinyl, tetrahydrothiopyranyl, 1-oxotetrahydrothiopyranyl and 1,1-dioxotetrahydrothiopyranyl wherein the linkage of the heterocyclic ring to the amidocarbonyl moiety can occur at a carbon atom or divalent nitrogen atom of the heterocyclic ring and wherein said substituent for any of said heterocyclic rings are one or more of alkyl, alkylcarbonyl, carboxyl, carboxyalkyl, carboxyaralkyl, aralkyl, aralkylcarbonyl, aralkoxycarbonyl, alkoxycarbonyl, alkoxycarbonylalkyl, aminoalkylcarbonyl, cyano, alkylsulfonyl, alkoxycarbonylaminoalkylcarbonyl, oxo or unsubstituted or substituted amino wherein said substituent is one or more of alkyl, carboxyalkyl, alkoxycarbonyl or alkoxycarbonylalkyl or
(11) unsubstituted or substituted alkyl, wherein said substituent is one or more of hydroxyl, alkoxy, carboxyl, phenyl, hydroxyphenyl, alkylphenyl, carboxyalkylphenyl, cyano, alkylsulfonyl, acetamidino, formamidino, aminocarbonyl, alkylaminocarbonyl, aralkyl, aralkoxycarbonyl, halogen, thio, alkylthio, alkoxycarbonyl, alkoxycarbonylalkyl, Het, or unsubstituted or substituted amino, wherein said substituent is one or more of alkyl, deuterated alkyl, piperidinyl, Cyc, pyridinyl, morpholinyl, tetrahydropyranyl, tetrahydrothiapyranyl, tetrahydrothiapyranyl S-oxide, alkoxycarbonylpiperidinyl, cyano, cyanoalkyl, hydroxyalkyl, haloalkyl, dialkyl, alkylcarbonyl, carboxyl, alkylsulfonyl, carboxyalkyl, alkoxycarbonyl, alkoxycarbonylalkyl, aralkoxycarbonyl, aminoalkyl, aminocarbonyl, aminocarbonylalkyl, alkylaminocarbonyl, phenalkyl or unsubstituted or substituted alkylcarbonyl, where said substituent is a 5-membered heterocyclic ring having 1 or 2 heteroatoms and where said heteroatom is N, Cyc is defined as unsubstituted or substituted cycloalkyl wherein said substituent is alkoxycarbonyl, carboxyl, hydroxyl, oxo or spiro-dioxolanyl and Het is defined as unsubstituted or substituted heterocyclic rings selected from the group consisting of: pyrrolidinyl, imidazolyl, 1,2,4-triazolyl, tetrazolyl, tetrahydrofuranyl, furanyl, 1,3-dioxolanyl, thienyl, piperidinyl, piperazinyl, pyridinyl, quinuclidinyl, morpholinyl, 1,3-tetrahydrothiazinyl, hexahydroazepinyl, tetrahydropyranyl, tetrahydrothipyranyl, 1-oxotetrahydrothiopyranyl and 1,1-dioxotetrahydrothiopyranyl wherein the linkage of the heterocyclic ring to the alkyl moiety can occur at a carbon atom or divalent nitrogen atom of the heterocyclic ring; and wherein said substituent for any of said heterocyclic rings are one or more of alkyl, amino, carboxyl, carboxyalkyl, aralkyl, carboxyaralkyl, alkoxycarbonyl, halogen substituted alkoxycarbonyl, alkoxycarbonylalkyl, alkoxyalkyl, alkoxyalkoxyalkyl, alkoxyalkoxyalkoxyalkyl, aralkylcarbonyl, aralkoxyalkyl, phenyl, aralkoxycarbonyl, oxo, $SO_3H$, or unsubstituted or substituted amino wherein said substituent is alkyl, carboxyl, carboxyalkyl, alkoxycarbonyl or alkoxycarbonylalkyl;

$R^{14}$ and $R^{15}$ are independently (1) hydrogen, (2) unsubstituted or substituted alkyl where said substituent is one or more of hydrogen, carboxyl, amino, aminoalkylamino, aminocarbonyl, hydroxyl, alkoxyl, alkylthio, thioalkyl, alkylsulfinyl, alkylsulfonyl, phenylalkoxycarbonyl, alkoxycarbonyl, indolyl, phenalkyl, hydroxyphenalkyl or unsubstituted 5-membered saturated heterocyclic rings having 1 or 2 hetero atoms wherein said hetero atom is N or (3) heterocyclic rings selected from the group consisting of: unsubstituted or substituted saturated or unsaturated rings having 5, 6, 7 or 8 total members and 1, 2, 3 or 4 N heteroatoms; having 5 or 6 total members and 1 or 2 O heteroatoms; having 5 or 6 total members and 1 S heteroatom; or having 6 total members and 2 different heteroatoms from the group consisting of N, 0 or S and wherein said substituent is one or more of alkyl, oxo, carboxyl, phenylalkyl, carboxyphenylalkyl or alkoxycarbonyl; and m and n are integers of from 0 to 1; and the pharmaceutically acceptable salts thereof.

In one embodiment is the method of controlling the timing of estrus, wherein the compound has the formula

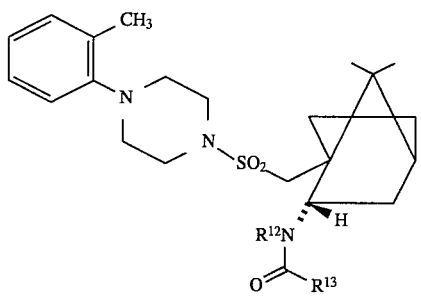

wherein
$R^{12}$ is (1) hydrogen, (2) alkoxycarbonyl or (3) unsubstituted of substituted alkyl wherein said substituent is hydroxyl, alkoxyl, carboxyl, carboxyalky, alkylsulfonyl or alkoxycarbonyl;

$R^{13}$ is (1) hydrogen, (2) alkoxyl, (3) aralkoxyl, (4) alkoxycarbonyl, (5) alkoxycarbonylamino, (6) unsubstituted or substituted cycloalkyl, wherein said substituent is carboxyl, (7) unsubstituted or substituted phenyl wherein said substituent is one or more of carboxyl, carboxyalkyl or $SO_3H$, (8) unsubstituted or substituted amino, wherein said substituent is unsubstituted or substituted alkyl where said substituent is one or more of carboxyl, alkylsulfonyl or unsubstituted 5-membered heterocyclic rings having 1 or 2 heteroatoms, where said heteroatom is N, (9) unsubstituted or substituted heterocyclic rings of the Formulae

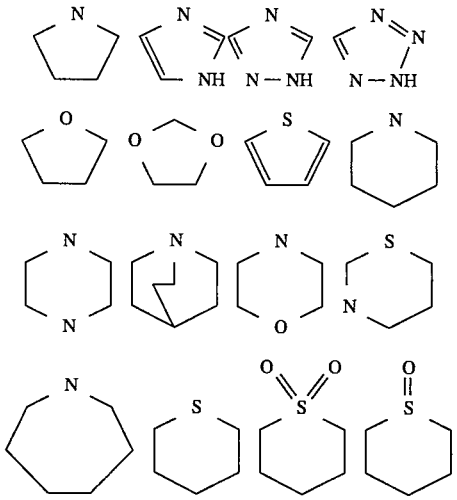

wherein the linkage of the heterocyclic ring to the amidocarbonyl moiety can occur at a carbon atom or divalent nitrogen atom of the heterocyclic ring and where said substituents on said heterocyclic ring are one or more of alkyl, carboxyl, carboxyalkyl, carboxyaralkyl, aralkylcarbonyl, aralkoxy-carbonyl, alkoxycarbonyl, alkoxycarbonylalkyl, alkoxy-carbonylaminoalkylcarbonyl, oxo or unsubstituted or substituted amino wherein said substituent is one or more of alkyl, carboxylalkyl, alkoxycarbonyl or alkoxycarbonylalkyl or

(10) unsubstituted or substituted alkyl, wherein said substituent is one or more of hydroxyl, carboxyl, carboxyalkylphenyl, alkylsulfonyl, aminocarbonyl, alkylaminocarbonyl, aralkyl, aralkoxycarbonyl, halogen, alkoxycarbonyl, alkoxycarbonylalkyl, Het or unsubstituted or substituted amino, wherein said substituent is one or more of alkyl, deuterated alkyl, cyanoalkyl, hydroxyalkyl, haloalkyl, dialkyl, alkylcarbonyl, alkylsulfonyl, carboxyalkyl, aminoalkyl, Cyc, piperidinyl, alkoxycarbonylpiperidinyl, pyridinyl, tetrahydropyranyl, tetrahydrothiopyranyl, tetrahydrothiopyranyl S-oxide, alkoxycarbonyl, alkoxycarbonylalkyl, aralkoxycarbonyl, aminocarbonylalkyl, alkylaminocarbonyl, phenalkyl or unsubstituted or substituted alkylcarbonyl, where said substituent is a 5-membered heterocyclic ring having 1 heteroatom and where said hetero atom is N, where Cyc is defined as substituted or unsubstituted cycloalkyl wherein said substituent is alkoxycarbonyl, carboxyl, hydroxyl, oxo or spiro-di-oxolanyl and Het is defined as unsubstituted or substituted heterocyclic rings of the Formulae

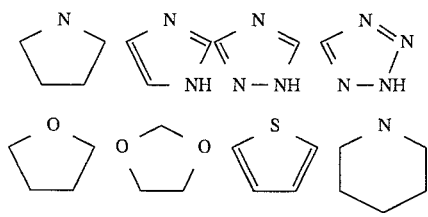

-continued

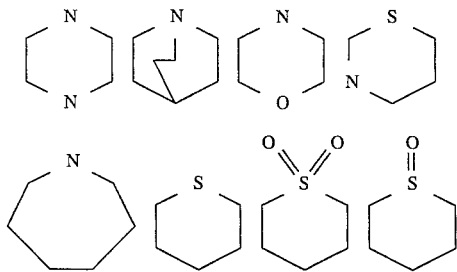

wherein the linkage of the heterocyclic ring to the alkyl moiety can occur at a carbon atom or divalent nitrogen atom of the heterocyclic ring and where said substituent on said heterocyclic ring is one or more of alkyl, amino, carboxyl, carboxyalkyl, carboxyaralkyl, alkoxycarbonyl, halogen substituted alkoxycarbonyl, alkoxycarbonylalkyl, alkoxyalkoxyalkyl, alkoxyalkoxyalkoxyalkyl, aralkylcarbonyl, aralkoxyalkyl, aralkoxyalkyl, aralkoxycarbonyl, oxo, SO$_3$H, or unsubstituted or substituted amino wherein said substituent is alkyl, carboxyalkyl, alkoxycarbonyl or alkoxycarbonylalkyl.

In a class is the method of controlling the timing of estrus, wherein administration of the compound begins prior to expected estrus.

In a subclass of the invention is the method of controlling the timing of estrus, wherein the compound is administered orally to the farm animal at a daily dosage of 1 to 100 mg/kg.

DETAILED DESCRIPTION OF THE INVENTION

The present invention provides a method of increasing pregnancy rates in farm animals by administering piperazinylcamphorsulfonyl oxytocin receptor antagonists of formula I. In addition, the present invention provides a method of increasing survival of farm animal neonates by controlling the timing of parturition so that delivery of the neonates occurs during the daylight hours, thereby ensuring that proper monitoring of the neonates will occur. Additionally, the present invention provides a method of controlling the timing of estrus in a farm animal so that estrus can be synchronized amongst a group of farm animals, thereby allowing for easier farm management.

The oxytocin receptor antagonist compounds of formula I can be prepared according to the methods disclosed in EP 532,097, published Mar. 17, 1993. The compound disclosed in Example 36 of EP 532,097, i.e., 1-((7,7-Dimethyl-2-endo-(2S-amino-4-(methylsulfonyl)-butyramido)-bicyclo(2.2.1)-heptan-1-yl)methanesulfonyl)-4-(2-methylphenyl)piperazine, is particularly preferred in the instant invention and will hereafter be referred to as Compound A.

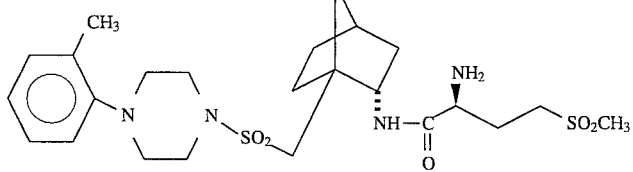

Compound A

Crystalline salts of Compound A, as well as an improved process for making Compound A and the crystalline salts of Compound A, are described in EP Patent Publication No. 614,894, published Sep. 14, 1994. The compound disclosed in Example 37 of EP 532,097, i.e., 1-((7,7-Dimethyl-2-endo-(2S-(imidazol-4-ylacetyl-amino)-4-(methylsulfonyl)butyramido)-bicyclo(2.2.1)-heptan-1-yl)methanesulfonyl)- 4-(2-methylphenyl)piperazine, is also useful in the methods of the instant invention and will hereafter be referred to as Compound B.

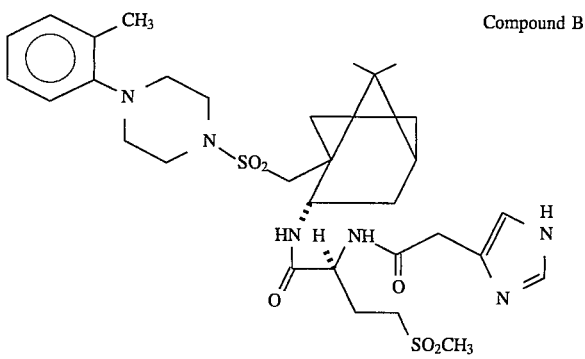

Compound B

As used herein, the terms "farm animal," domestic "livestock" and "livestock" are synonymous and are intended to include cows, pigs, sheep and goats.

The terms "newborns" and "neonates," as used herein are synonymous and refer to newly born animals.

The term "parturition," as used herein, means the act or process of giving birth to offspring.

The term "delivery," as used herein, refers to the expulsion or extraction of the offspring and the after birth.

The period of gestation for each of the species of farm animal of the present invention is well known to those of ordinary skill in the art. That is, an ordinarily skilled farmer, veterinarian and/or researcher will know the expected length of pregnancy for each species and can therefore readily determine the expected day of delivery of the offspring calculated from the day when mating occurred.

The length of the estrus cycle for each of the species of farm animal of the present invention is well known to those of ordinary skill in the art. Moreover, an ordinarily skilled farmer, veterinarian and/or researcher, by careful observation and recordkeeping during routine farm management, will know when onset of estrus is expected for each individual farm animal.

Salts encompassed within the term "pharmaceutically acceptable salts" refer to non-toxic salts of the compounds of this invention which are generally prepared by reacting the free base with a suitable organic or inorganic acid. Representative salts include the following salts:

| | |
|---|---|
| Acetate | Lactobionate |
| Benzenesulfonate | Laurate |
| Benzoate | Malate |
| Bicarbonate | Maleate |
| Bisulfate | Mandelate |
| Bitartrate | Mesylate |
| Borate | Methylbromide |
| Bromide | Methylnitrate |
| Calcium Edetate | Methylsulfate |
| Camsylate | Mucate |
| Carbonate | Napsylate |
| Chloride | Nitrate |
| Clavulanate | N-methylglucamine |
| Citrate | ammonium salt |
| Dihydrochloride | Oleate |
| Edetate | Oxalate |
| Edisylate | Pamoate (Embonate) |
| Estolate | Palmitate |
| Esylate | Pantothenate |
| Fumarate | Phosphate/diphosphate |
| Gluceptate | Polygalacturonate |
| Gluconate | Salicylate |
| Glutamate | Stearate |
| Glycollylarsanilate | Sulfate |
| Hexylresorcinate | Subacetate |
| Hydrabamine | Succinate |
| Hydrobromide | Tannate |
| Hydrochloride | Tartrate |
| Hydroxynaphthoate | Teoclate |
| Iodide | Tosylate |
| Isothionate | Triethiodide |
| Lactate | Valerate |

The term "pharmacologically effective amount" shall mean that amount of a drug or pharmaceutical agent that will elicit the biological or medical response of a tissue, system, animal or human that is being sought by a researcher or clinician.

The term "alkyl" shall mean straight or branched chain alkanes of one to ten total carbon atoms, or any number within this range.

The term "alkenyl" shall mean straight or branched chain alkenes with one or more degrees of unsaturation at any position on the chain, of two to ten total carbon atoms, or any number within this range.

The term "alkynyl" shall mean straight or branched chain alkynes with one or more degrees of unsaturation at any position on the chain, of two to ten total carbon atoms, or any number within this range.

The term "aryl" shall mean phenyl, naphthyl or fluorenyl.

The term "cycloalkyl" shall mean cyclic rings of alkanes of three to eight total carbon atoms.

The term "alkoxy" or "alkoxyl" shall mean straight or branched chain alkoxy groups of one to ten total carbon atoms, or any number within this range.

The term "trihaloalkylsulfonyloxo" shall mean the substituent

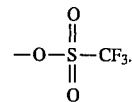

Whenever the terms "alkyl" or "aryl" or either of their prefix roots appear in a name of a substituent (e.g., aralkoxyaryloxy) they shall be interpreted as including those limitations given above for "alkyl" and "aryl". Designated numbers of carbon atoms (e.g., $C_{1-10}$) shall refer independently to the number of carbon atoms in an alkyl or cyclic alkyl moiety or to the alkyl portion of a larger substituent in which alkyl appears as its prefix root.

The term "oxo" shall refer to the substituent =O.

The term "halogen" shall include iodine, bromine, chlorine and fluorine.

The term "substituted" shall be deemed to include multiple degrees of substitution by a named substitutent.

Where multiple substituent moieties are disclosed or claimed, the substituted compound can be independently substituted by one or more of the disclosed or claimed substituent moieties, singly or plurally.

Where a heterocyclic ring is substituted, the linkage of the substituent to the heterocyclic ring can occur at a carbon atom or a divalent nitrogen atom of the heterocyclic ring.

The compounds of the present invention can be administered in such oral dosage forms as tablets, capsules (each including timed release and sustained release formulations), pills, powders, granules, elixirs, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed.

The dosage regimen utilizing the compounds of the present invention is selected in accordance with a variety of factors including type, species, age, weight, sex and medical condition of the animal; the severity of the condition to be treated; the route of administration; the renal and hepatic function of the animal; and the particular compound or salt thereof employed. An ordinarily skilled farmer, veterinarian or researcher can readily determine and prescribe the effective amount of the drug required to obtain the desired therapeutic effect.

Oral dosages of the present invention, when used for the indicated effects, will range between about 1 to 100 mg/kg/day orally. Intravenously, the most preferred doses will range from 0.5 to about 50 mg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, zanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carders to which the compound molecules are coupled. The compounds of the present invention may also be coupled with soluble polymers as targetable drug carriers. Such polymers can include polyvinylpyrrolidone, pyran copolymer, polyhydroxypropyl-methacrylamide-phenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

For parenteral administration, sterile suspensions and solutions are desired.

The compounds of the present invention, may have asymmetric centers and occur as racemates, racemic mixtures and as individual diastereomers, or enantiomers with all isomeric forms being included in the present invention. Therefore, where a compound is chiral, the separate enantiomers, substantially free of the other, are included within the scope of the invention; further included are all mixtures of the two enantiomers. Also included within the scope of the invention are polymorphs and hydrates of the compounds of the instant invention.

To improve fertility in a farm animal, a mated animal, for example, a mated ewe, is treated with an oxytocin antagonist of formula I beginning on between day 10 to day 15 after onset of estrus. The compound of formula I is administered to the mated animal for a period of one day to three weeks, preferably one week to three weeks, most preferably one week to two weeks. In one embodiment of the present invention, the oxytocin antagonist compound of formula I is administered to the farm animal beginning on between day 12 and day 15 after mating and fertilization for a period of one day to three weeks, preferably, one week to three weeks, most preferably, one week to two weeks.

A dose of 1 to 100 mg/kg/day is effective to supplement the natural signal from the conceptus to ensure maternal recognition of pregnancy, thereby preventing or reducing the rate of embryonic loss. Preferably, a dose of 1 to 20 mg/kg/day is employed in the method of the present invention. The compounds of formula I are administered orally or parenterally (e.g., subcutaneously or intravenously). Most preferably, the compound is administered orally. Administration of a compound of formula I, as described above, results in increased fertility and embryonic survival by prolonging the corpus luteum; thus, pregnancy rates in farm animals are enhanced.

In a preferred embodiment of the present invention, Compound A is administered, as described above, to enhance fertility and embryonic survival of the farm animal. More specifically, Compound A is administered to a mated farm animal beginning on between day 10 and day 15, preferably between day 12 and day 15, of the estrous cycle after mating. Compound A is administered to the mated farm animal for a period of one day to three weeks, preferably one week to three weeks, most preferably one week to two weeks, at a daily dosage of I to 100 mg/kg, preferably 1 to 20 mg/kg. Compound A is preferably administered to the farm animal orally. In a second embodiment, Compound B is administered, as described above for Compound A, to enhance fertility and embryonic survival of the farm animal.

The compounds of formula I, and in particular, Compounds A and B, are also useful for controlling the timing of parturition in farm animals. An oxytocin antagonist of formula I is administered to the mother on the evening before expected delivery to delay parturition so that the delivery occurs during the daylight hours. By delaying the timing of parturition, proper monitoring of the delivery and the neonates is ensured resulting in increased survival rates of the newborns. A dose of 1 to 100 mg/kg/day is effective to control the timing of parturition to the daylight hours. Preferably, a dose of 1 to 20 mg/kg/day is used The compounds of formula I are administered orally or parenterally (e.g., subcutaneously or intravenously). Preferably, the compound is administered orally.

In a preferred embodiment, Compound A is employed as described to control the timing of parturition in farm animals. More specifically, Compound A is administered to a farm animal which is expected to deliver a neonate within 24 hours on the evening before the expected delivery in a daily dose of 1 to 100 mg/kg, preferably 1 to 20 mg/kg, to delay parturition to the daytime when the neonate can be monitored, thereby increasing the chance of survival. In another embodiment, Compound B is administered, as previously described for Compound A, to control the timing of parturition in farm animals.

Additionally, the compounds of formula I, and in particular Compounds A and B, are also useful for controlling the timing of estrus in farm animals. An oxytocin antagonist of formula I (e.g., Compound A, Compound B) is administered to a cycling farm animal prior to expected estrus to prevent regression of the corpus luteum. The compound is administered orally or parenterally (e.g., intravenously or subcutaneously) at a daily dosage of 1 to 100 mg/kg, preferably 1 to 20 mg/kg, to prevent corpus luteal regression and retard estrus; daily administration of the compound will retard estrus until administration of the compound ceases. Preferably, the oxytocin antagonist compound is administered at least 1 day prior to expected estrus. More preferably, the compound is administered daily between 1 day and two weeks prior to expected estrus to prevent corpus luteal regression and retard estrus until administration of the compound ceases. By delaying estrus in a group of farm animals, a farmer can synchronize estrus among the group to provide time and cost savings in farm management.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A method of increasing fertility and embryonic survival in a farm animal, comprising administering to a farm animal, in which fertilization has occurred, just prior to or during the period of maternal recognition of pregnancy a pharmacologically effective amount of a compound of formula I wherein
X is
(1) C or
(2) N;
Y is
(1) carbonyl or
(2) sulfonyl;
Z is an optional substituent that, when present, is substituted or unsubstituted alkyl where said substituent is carboxyl;
$R^1$ is
(1) hydrogen,
(2) alkyl or
(3) $NH_2$;
$R^2$ is hydrogen, or
$R^1$ and $R^2$ together are bridged alkyl of three or four methylenes;
$R^3$ and $R^4$ are independently one or more of
(1) hydrogen,
(2) halogen,
(3) alkylsulfonyl,
(4) alkoxy or
(5) unsubstituted or substituted alkyl wherein said substituent is hydroxyl, alkoxyl, alkylsulfonyl, amino, alkylamino or dialkylamino;
$R^5$ and $R^6$ are independently selected from
(1) hydrogen,
(2) alkyl,
(3) substituted alkyl where said substituent is amino, hydroxyl, alkoxyl, alkylsulfonyl, arylsulfonyl, alkylamino or dialkylamino,
(4) phenylalkyl or
(5) oxo;
$R^7$ and $R^8$ are independently one or more of
(1) hydrogen,
(2) alkyl or
(3) joined together to form unsubstituted or substituted cycloalkyl where said substituent is hydroxy or hydroxyalkyl;
$R^9$ and $R^{10}$ am independently selected from
(1) hydrogen,
(2) hydroxyl,
(3) halogen,
(4) oximino,
(5) methyl,
(6) carboxyl,
(7) oxo,
(8) alkoxycarbonyl,
(9) alkylcarbonyloxy,
(10) alkoxycarbonylalkoxy,
(11) trihaloalkylsulfonyloxo or
(12) unsubstituted or substituted amino where said substituent is one or more of alkyl, carboxyalkyl or alkoxycarbonylalkyl; or
$R^9$ and $R^{10}$ are together joined to form a cyclic epoxide, whereby the $R^9$ and $R^{10}$ substituents are on the same carbon or on adjacent carbon atoms;
$R^{11}$ is
(1) hydrogen,
(2) —N($R^{12}$)—CO—$R^{13}$ or
(3) —CO—N($R^{14}$)$R^{15}$;
$R^{12}$ is
(1) hydrogen,
(2) alkoxy,
(3) unsubstituted or substituted alkyl where said substituent is one or more of carboxyl, hydroxyl, alkoxyl, alkoxycarbonyl, alkylsulfonyl or arylsulfonyl,
(4) alkoxycarbonyl,
(5) alkoxycarbonylamino or
(6) alkylsulfonylalkyl;
$R^{13}$ is
(1) hydrogen,
(2) alkoxyl,
(3) aralkoxyl,
(4) carboxyl,
(5) alkoxycarbonyl, (6) alkoxycarbonylamino,
(7) unsubstituted or substituted cycloalkyl, wherein said substituent is carboxyl,
(8) unsubstituted or substituted phenyl wherein said substituent is one or more of carboxyl, carboxyalkyl or SO₃H,
(9) unsubstituted or substituted amino, wherein said substituent is unsubstituted or substituted alkyl where said substituent is one or more of carboxyl, alkylsulfonyl or unsubstituted 5-membered heterocyclic rings having 1 or 2 heteroatoms, where said heteroatom is N,
(10) unsubstituted or substituted heterocyclic rings selected from the group consisting of: pyrrolidinyl, imidazolyl, 1,2,4-triazolyl, tetrazolyl, tetrahydrofuranyl, furanyl, 1,3-dioxolanyl, thienyl, piperidinyl, piperazinyl, quinuclidinyl, morpholinyl, 1,3-tetrahydrothiazinyl, hexahydroazepinyl, tetrahydrothiopyranyl, 1-oxotetrahydrothiopyranyl and 1,1-dioxotetrahydrothiopyranyl wherein the linkage of the heterocyclic ring to the amidocarbonyl moiety can occur at a carbon atom or divalent nitrogen atom of the heterocyclic ring and wherein said substituent for any of said heterocyclic rings are one or more of alkyl, alkylcarbonyl, carboxyl, carboxyalkyl, carboxyaralkyl, aralkyl, aralkylcarbonyl, aralkoxycarbonyl, alkoxycarbonyl, alkoxycarbonylalkyl, aminoalkylcarbonyl, cyano, alkylsulfonyl, alkoxycarbonylaminoalkylcarbonyl, oxo or unsubstituted or substituted amino wherein said substituent is one or more of alkyl, carboxyalkyl, alkoxycarbonyl or alkoxycarbonylalkyl or
(11) unsubstituted or substituted alkyl, wherein said substituent is one or more of hydroxyl, alkoxy, carboxyl, phenyl, hydroxyphenyl, alkylphenyl, carboxyalkylphenyl, cyano, alkylsulfonyl, acetamidino, formamidino, aminocarbonyl, alkylaminocarbonyl, aralkyl, aralkoxycarbonyl, halogen, thio, alkylthio, alkoxycarbonyl, alkoxycarbonylalkyl, Het, or unsubstituted or substituted amino, wherein said substituent is one or more of alkyl, deuterated alkyl, piperidinyl, Cyc, pyridinyl, morpholinyl, tetrahydropyranyl, tetrahydrothiapyranyl, tetrahydrothiapyranyl S-oxide, alkoxycarbonylpiperidinyl, cyano, cyanoalkyl, hydroxyalkyl, haloalkyl, dialkyl, alkylcarbonyl, carboxyl, alkylsulfonyl, carboxyalkyl, alkoxycarbonyl, alkoxy-carbonylalkyl, aralkoxycarbonyl, aminoalkyl, amino-carbonyl, aminocarbonylalkyl, alkylaminocarbonyl, phenalkyl or unsubstituted or substituted alkylcarbonyl, where said substituent is a 5-membered heterocyclic ring having 1 or 2 heteroatoms and where said heteroatom is N, Cyc is defined as unsubstituted or substituted cycloalkyl wherein said substituent is alkoxycarbonyl, carboxyl, hydroxyl, oxo or spirodioxolanyl and Het is defined as unsubstituted or substituted heterocyclic rings selected from the group consisting of: pyrrolidinyl, imidazolyl, 1,2,4-triazolyl, tetrazolyl, tetrahydrofuranyl, furanyl, 1,3-dioxolanyl, thienyl, piperidinyl, piperazinyl, pyridinyl, quinuclidinyl, morpholinyl, 1,3-tetrahydrothiazinyl, hexahydroazepinyl, tetrahydropyranyl, tetrahydrothio-pyranyl, 1-oxotetrahydrothiopyranyl and 1,1-dioxo-tetrahydrothiopyranyl wherein the linkage of the heterocyclic ring to the alkyl moiety can occur at a carbon atom or divalent nitrogen atom of the heterocyclic ring; and wherein said substituent for any of said heterocyclic rings are one or more of alkyl, amino, carboxyl, carboxyalkyl, aralkyl, carboxyaralkyl, alkoxycarbonyl, halogen substituted alkoxycarbonyl, alkoxycarbonylalkyl, alkoxyalkyl, alkoxyalkoxyalkyl, alkoxyalkoxyalkoxyalkyl, aralkylcarbonyl, aralkoxyalkyl, phenyl, aralkoxycarbonyl, oxo, SO₃H, or unsubstituted or substituted amino wherein said substituent is alkyl, carboxyl, carboxyalkyl, alkoxycarbonyl or alkoxycarbonylalkyl;

R¹⁴ and R¹⁵ are independently
(1) hydrogen,
(2) unsubstituted or substituted alkyl where said substituent is one or more of hydrogen, carboxyl, amino, aminoalkyl-amino, aminocarbonyl, hydroxyl, alkoxyl, alkylthio, thioalkyl, alkylsulfinyl, alkylsulfonyl, phenylalkoxy-carbonyl, alkoxycarbonyl, indolyl, phenalkyl, hydroxy-phenalkyl or unsubstituted 5-membered saturated heterocyclic rings having 1 or 2 hetero atoms wherein said hetero atom is N or
(3) heterocyclic rings selected from the group consisting of: unsubstituted or substituted saturated or unsaturated rings having 5, 6, 7 or 8 total members and 1, 2, 3 or 4 N heteroatoms; having 5 or 6 total members and 1 or 2 O heteroatoms; having 5 or 6 total members and 1 S heteroatom; or having 6 total members and 2 different heteroatoms from the group consisting of N, O or S and wherein said substituent is one or more of alkyl, oxo, carboxyl, phenylalkyl, carboxyphenylalkyl or alkoxycarbonyl; and m and n are integers of from 0 to 1; and the pharmaceutically acceptable salts thereof.

2. The method of claim 1, wherein the compound has the formula

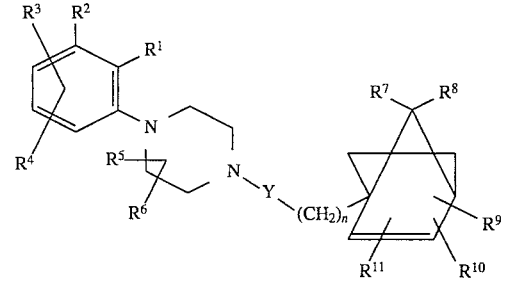

wherein
R¹¹ is
(1) —N(R¹²)—CO—R¹³ or
(2) —CO—N(R¹⁴)—R¹⁵; and
R¹³ is
(1) hydrogen,
(2) alkoxyl,
(3) aralkoxyl,
(4) carboxyl,
(5) alkoxycarbonyl,
(6) alkoxycarbonylamino,
(7) unsubstituted or substituted cycloalkyl, wherein said substituent is carboxyl,
(8) unsubstituted or substituted phenyl wherein said substituent is one or more of carboxyl, carboxyalkyl or SO₃H, (9) unsubstituted or substituted amino, wherein said substituent is unsubstituted or substituted alkyl where said substituent is one or more of carboxyl, alkylsulfonyl or unsubstituted 5-membered heterocyclic rings having 1 or 2 heteroatoms, where said heteroatom is N,

(10) unsubstituted or substituted heterocyclic rings selected from the group consisting of: pyrrolidinyl, imidazolyl, 1,2,4-triazolyl, tetrazolyl, tetrahydrofuranyl, furanyl, 1,3-dioxolanyl, thienyl, piperidinyl, piperazinyl, quinuclidinyl, morpholinyl, 1,3-tetrahydrothiazinyl, hexahydroazepinyl, tetrahydrothiopyranyl, 1-oxotetrahydrothiopyranyl and 1,1-dioxotetrahydrothiopyranyl wherein the linkage of the heterocyclic ring to the amidocarbonyl moiety can occur at a carbon atom or divalent nitrogen atom of the heterocyclic ring and wherein said substituent for any of said heterocyclic rings are one or more of alkyl, alkylcarbonyl, carboxyl, carboxyalkyl, carboxyaralkyl, aralkyl, aralkylcarbonyl, aralkoxy-carbonyl, alkoxycarbonyl, alkoxycarbonylalkyl, aminoalkylcarbonyl, cyano, alkylsulfonyl, alkoxycarbonyl-aminoalkylcarbonyl, oxo or unsubstituted or substituted amino wherein said substituent is one or more of alkyl, carboxyalkyl, alkoxycarbonyl or alkoxycarbonylalkyl or

(11) unsubstituted or substituted alkyl, wherein said substituent is one or more of hydroxyl, alkoxy, carboxyl, phenyl, hydroxyphenyl, alkylphenyl, carboxyalkylphenyl, cyano, alkylsulfonyl, acetamidino, formamidino, aminocarbonyl, alkylaminocarbonyl, aralkyl, aralkoxycarbonyl, halogen, thio, alkylthio, alkoxycarbonyl, alkoxycarbonylalkyl, Het, or unsubstituted or substituted amino, wherein said substituent is one or more of alkyl, deuterated alkyl, piperidinyl, Cyc, pyridinyl, morpholinyl, tetrahydropyranyl, tetrahydrothiapyranyl, tetrahydrothiapyranyl S-oxide, alkoxycarbonylpiperidinyl, cyano, cyanoalkyl, hydroxyalkyl, haloalkyl, dialkyl, alkylcarbonyl, carboxyl, alkylsulfonyl, carboxyalkyl, alkoxycarbonyl, alkoxycarbonylalkyl, aralkoxycarbonyl, aminoalkyl, aminocarbonyl, aminocarbonylalkyl, alkylaminocarbonyl, phenalkyl or unsubstituted or substituted alkylcarbonyl, where said substituent is a 5-membered heterocyclic ring having 1 heteroatom and where said heteroatom is N; Cyc is defined as unsubstituted or substituted cycloalkyl wherein said substituent is alkoxycarbonyl, carboxyl, hydroxyl, oxo or spiro-dioxolanyl and Het is defined as unsubstituted or substituted heterocyclic rings selected from the group consisting of: pyrrolidinyl, imidazolyl, 1,2,4-triazolyl, tetrazolyl, tetrahydrofuranyl, furanyl, 1,3-dioxolanyl, thienyl, piperidinyl, piperazinyl, pyridinyl, quinuclidinyl, morpholinyl, 1,3-tetrahydrothiazinyl, hexahydroazepinyl, tetrahydropyranyl, tetrahydrothiopyranyl, 1-oxotetrahydrothiopyranyl and 1,1-dioxotetrahydrothiopyranyl wherein the linkage of the heterocyclic ring to the alkyl moiety can occur at a carbon atom or divalent nitrogen atom of the heterocyclic ring; and wherein said substituent for any of said heterocyclic rings are one or more of alkyl, amino, carboxyl, carboxyalkyl, aralkyl, carboxyaralkyl, alkoxycarbonyl, halogen substituted alkoxycarbonyl, alkoxycarbonylalkyl, alkoxyalkyl, alkoxyalkoxyalkyl, alkoxyalkoxyalkoxyalkyl, aralkylcarbonyl, aralkoxyalkyl, phenyl, aralkoxycarbonyl, oxo, SO$_3$H, or unsubstituted or substituted amino wherein said substituent is alkyl, carboxyl, carboxyalkyl, alkoxycarbonyl or alkoxycarbonylalkyl.

3. The method of claim 2, wherein the compound has the formula

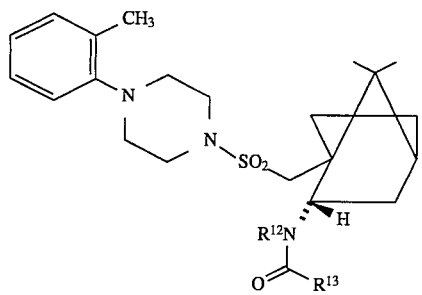

wherein
R$^{12}$ is
(1) hydrogen,
(2) alkoxycarbonyl or
(3) unsubstituted of substituted alkyl wherein said substituent is hydroxyl, alkoxyl, carboxyl, carboxyalky, alkylsulfonyl or alkoxycarbonyl;

R$^{13}$ is
(1) hydrogen,
(2) alkoxyl,
(3) aralkoxyl,
(4) alkoxycarbonyl,
(5) alkoxycarbonylamino,
(6) unsubstituted or substituted cycloalkyl, wherein said substituent is carboxyl,
(7) unsubstituted or substituted phenyl wherein said substituent is one or more of carboxyl, carboxyalkyl or SO$_3$H, unsubstituted or substituted amino, wherein said substituent is unsubstituted or substituted alkyl where said substituent is one or more of carboxyl, alkylsulfonyl or unsubstituted 5-membered heterocyclic rings having 1 or 2 heteroatoms, where said heteroatom is N,
(9) unsubstituted or substituted heterocyclic rings of the Formulae

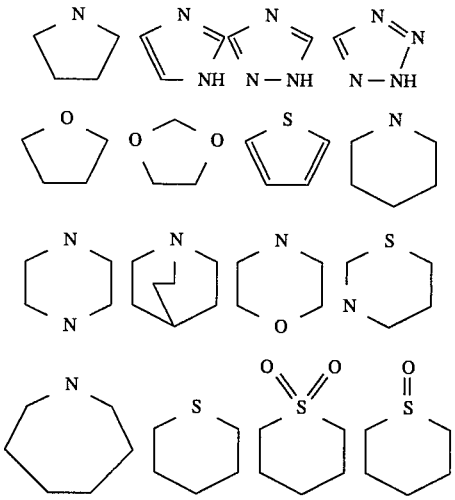

wherein the linkage of the heterocyclic ring to the amidocarbonyl moiety can occur at a carbon atom or divalent nitrogen atom of the heterocyclic ring and where said substituents on said heterocyclic ring are one or more of alkyl, carboxyl, carboxyalkyl, carboxyaralkyl, aralkylcarbonyl, aralkoxy-carbonyl, alkoxycarbonyl, alkoxycarbonylalkyl, alkoxy-carbonylaminoalkylcarbonyl, oxo or unsubstituted or substituted amino wherein said substituent is one or more of alkyl, carboxylalkyl, alkoxycarbonyl or alkoxycarbonylalkyl or

(10) unsubstituted or substituted alkyl, wherein said substituent is one or more of hydroxyl, carboxyl, carboxyalkylphenyl, alkylsulfonyl, aminocarbonyl, alkylaminocarbonyl, aralkyl, aralkoxycarbonyl, halogen, alkoxycarbonyl, alkoxycarbonylalkyl, Het or unsubstituted or substituted amino, wherein said substituent is one or more of alkyl, deuterated alkyl, cyanoalkyl, hydroxyalkyl, haloalkyl, dialkyl, alkylcarbonyl, alkylsulfonyl, carboxyalkyl, aminoalkyl, Cyc, piperidinyl, alkoxycarbonylpiperidinyl, pyridinyl, tetrahydropyranyl, tetrahydrothiopyranyl, tetrahydrothiopyranyl S-oxide, alkoxycarbonyl, alkoxycarbonylalkyl, aralkoxycarbonyl, aminocarbonylalkyl, alkylaminocarbonyl, phenalkyl or unsubstituted or substituted alkylcarbonyl, where said substituent is a 5-membered heterocyclic ring having 1 heteroatom and where said hetero atom is N, where Cyc is defined as substituted or unsubstituted cycloalkyl wherein said substituent is alkoxycarbonyl, carboxyl, hydroxyl, oxo or spiro-dioxolanyl and Het is defined as unsubstituted or substituted heterocyclic rings of the Formulae

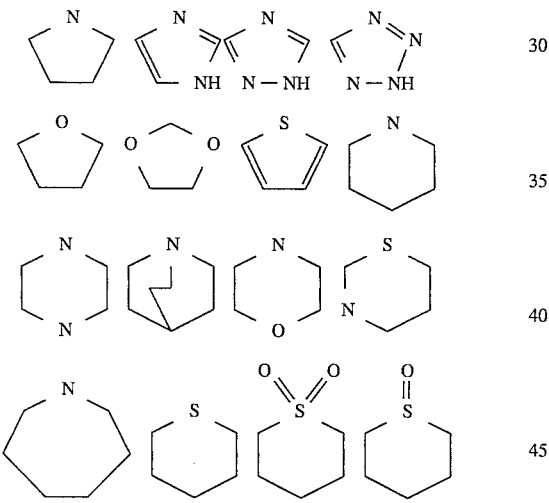

wherein the linkage of the heterocyclic ring to the alkyl moiety can occur at a carbon atom or divalent nitrogen atom of the heterocyclic ring and where said substituent on said heterocyclic ring is one or more of alkyl, amino, carboxyl, carboxyalkyl, carboxyaralkyl, alkoxycarbonyl, halogen substituted alkoxycarbonyl, alkoxycarbonylalkyl, alkoxyalkoxyalkyl, alkoxyalkoxyalkoxyalkyl, aralkylcarbonyl, aralkoxyalkyl, aralkoxyalkyl, aralkoxycarbonyl, oxo, SO$_3$H, or unsubstituted or substituted amino wherein said substituent is alkyl, carboxyalkyl, alkoxycarbonyl or alkoxycarbonylalkyl.

4. The method of claim 3, wherein
R$^{12}$ is
(1) hydrogen, or
(2) unsubstituted alkyl; and
R$^{13}$ is
(1) aralkoxyl, (2) unsubstituted or substituted heterocyclic rings of the Formulae

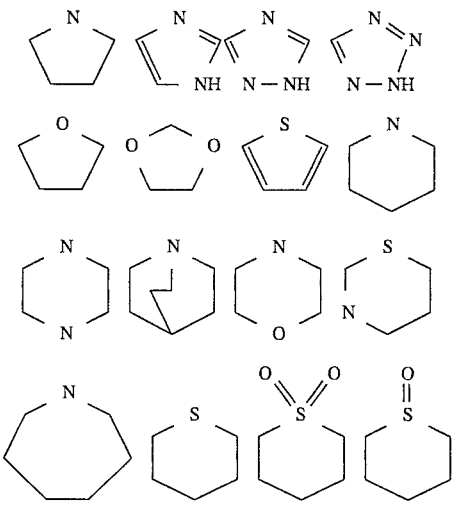

wherein the linkage of the heterocyclic ring to the amidocarbonyl moiety can occur at a carbon atom or divalent nitrogen atom of the heterocyclic ring and where said substituents on said heterocyclic ring are one or more of alkyl, carboxyl, carboxyalkyl, carboxyaralkyl, aralkylcarbonyl, aralkoxy-carbonyl, alkoxycarbonyl, alkoxycarbonylalkyl, alkoxy-carbonylaminoalkylcarbonyl, oxo or unsubstituted or substituted amino wherein said substituent is one or more of alkyl, carboxylalkyl, alkoxycarbonyl or alkoxycarbonylalkyl or (3) unsubstituted or substituted alkyl, wherein said substituent is one or more of hydroxyl, alkylsulfonyl, Het or unsubstituted or substituted amino, wherein said substituent is one or more of alkyl, deuterated alkyl, cyanoalkyl, hydroxyalkyl, haloalkyl, dialkyl, alkylcarbonyl, alkylsulfonyl, carboxyalkyl, aminoalkyl, Cyc, piperidinyl, alkoxycarbonylpiperidinyl, pyridinyl, tetrahydropyranyl, tetrahydrothiopyranyl, tetrahydrothiopyranyl S-oxide, alkoxycarbonyl or alkoxycarbonylalkyl; where Cyc is defined as substituted or unsubstituted cycloalkyl wherein said substituent is alkoxycarbonyl, carboxyl, and Het is defined as unsubstituted or substituted heterocyclic rings of the Formulae

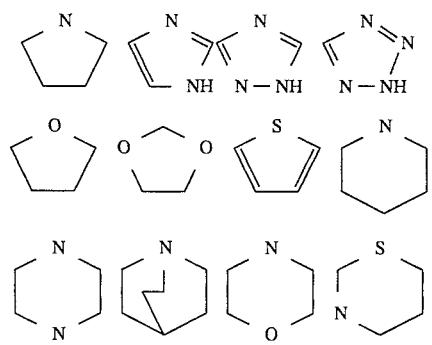

-continued

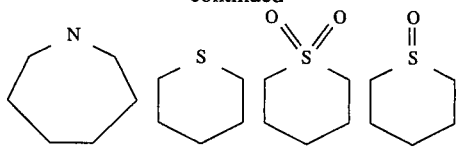

wherein the linkage of the heterocyclic ring to the alkyl moiety can occur at a carbon atom or divalent nitrogen atom of the heterocyclic ring and where said substituent on said heterocyclic ring is one or more of alkyl, amino, carboxyl, carboxyalkyl, carboxyaralkyl, alkoxycarbonyl, halogen substituted alkoxycarbonyl, alkoxycarbonylalkyl, alkoxyalkoxyalkyl, alkoxyalkoxyalkoxyalkyl, aralkylcarbonyl, aralkoxyalkyl, aralkoxyalkyl, aralkoxycarbonyl, oxo, $SO_3H$, or unsubstituted or substituted amino wherein said substituent is alkyl, carboxyalkyl, alkoxycarbonyl or alkoxycarbonylalkyl.

5. The method of claim 4, wherein the compound is

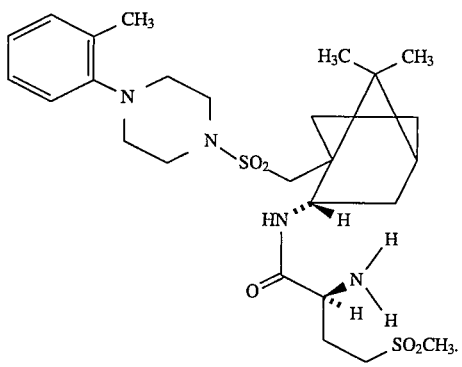

6. The method of claim 1, wherein the compound is administered at a daily dosage of 1 to 100 mg/kg.

7. The method of claim 6, wherein the daily dosage is 1 to 20 mg/kg.

8. The method of claim 1, wherein the compound is administered orally, subcutaneously or intravenously.

9. The method of claim 8, wherein the compound is administered orally.

10. The method of claim 1, wherein the compound is administered on between day 10 and day 15 of the estrous cycle after fertilization of the farm animal.

11. The method of claim 10, wherein the compound is administered on between day 12 and day 15 of the estrous cycle after fertilization.

12. The method of claim 10, wherein the compound is administered for a period of one day to three weeks.

13. The method of claim 12, wherein the compound is administered for a period of one week to three weeks.

14. The method of claim 13, wherein the compound is administered for a period of one week to two weeks.

15. The method of claim 12, wherein the compound is administered at a daily dosage of 1 to 100 mg/kg.

16. The method of claim 15, wherein the daily dosage is 1 to 20 mg/kg.

17. The method of claim 15, wherein the compound is administered orally.

18. The method of claim 15, wherein the compound is

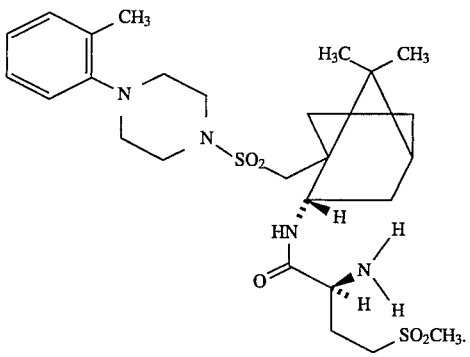

19. The method of claim 18, wherein the compound is administered orally.

20. The method of claim 1, wherein the increased fertility is accomplished by prolonging corpus luteal function for egg implantation.

21. The method of claim 20, wherein prolongation of corpus luteal function results in reduction of embryonic loss.

22. A method for improving survival of a farm animal neonate comprising controlling timing of parturition to effect delivery of the neonate during daylight hours by administering to a farm animal which is expected to deliver the neonate within 24 hours a pharmacologically effective amount of a compound of the formula I

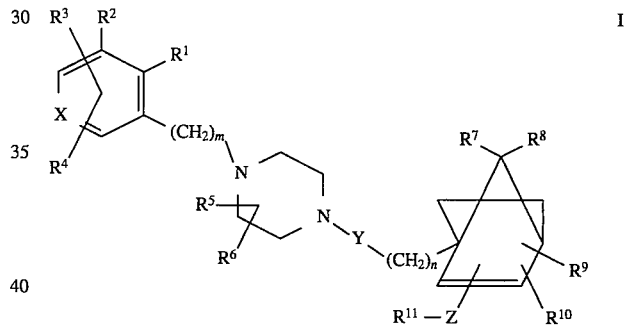

wherein

X is
  (1) C or
  (2) N;

Y is
  (1) carbonyl or
  (2) sulfonyl;

Z is an optional substituent that, when present, is substituted or unsubstituted alkyl where said substituent is carboxyl;

$R^1$ is
  (1) hydrogen,
  (2) alkyl or
  (3) $NH_2$;

$R^2$ is hydrogen, or $R^1$ and $R^2$ together are bridged alkyl of three or four methylenes;

$R^3$ and $R^4$ are independently one or more of
  (1) hydrogen,
  (2) halogen,
  (3) alkylsulfonyl,
  (4) alkoxy or
  (5) unsubstituted or substituted alkyl wherein said substituent is hydroxyl, alkoxyl, alkylsulfonyl, amino, alkylamino or dialkylamino;

$R^5$ and $R^6$ are independently selected from
  (1) hydrogen,
  (2) alkyl,
  (3) substituted alkyl where said substituent is amino, hydroxyl, alkoxyl, alkylsulfonyl, arylsulfonyl, alkylamino or dialkylamino,
  (4) phenylalkyl or
  (5) oxo;
$R^7$ and $R^8$ are independently one or more of
  (1) hydrogen,
  (2) alkyl or
  (3) joined together to form unsubstituted or substituted cycloalkyl where said substituent is hydroxy or hydroxyalkyl;
$R^9$ and $R^{10}$ are independently selected from
  (1) hydrogen,
  (2) hydroxyl,
  (3) halogen,
  (4) oximino,
  (5) methyl,
  (6) carboxyl,
  (7) oxo,
  (8) alkoxycarbonyl,
  (9) alkylcarbonyloxy,
  (10) alkoxycarbonylalkoxy,
  (11) trihaloalkylsulfonyloxo or
  (12) unsubstituted or substituted amino where said substituent is one or more of alkyl, carboxyalkyl or alkoxycarbonylalkyl; or
$R^9$ and $R^{10}$ are together joined to form a cyclic epoxide, whereby the $R^9$ and $R^{10}$ substituents are on the same carbon or on adjacent carbon atoms;
$R^{11}$ is
  (1) hydrogen,
  (2) —N($R^{12}$)—CO—$R^{13}$ or
  (3) —CO—N($R^{14}$)—$R^{15}$;
$R^{12}$ is
  (1) hydrogen,
  (2) alkoxy,
  (3) unsubstituted or substituted alkyl where said substituent is one or more of carboxyl, hydroxyl, alkoxyl, alkoxycarbonyl, alkylsulfonyl or arylsulfonyl,
  (4) alkoxycarbonyl,
  (5) alkoxycarbonylamino or
  (6) alkylsulfonylalkyl;
$R^{13}$ is
  (1) hydrogen,
  (2) alkoxyl,
  (3) aralkoxyl,
  (4) carboxyl,
  (5) alkoxycarbonyl,
  (6) alkoxycarbonylamino,
  (7) unsubstituted or substituted cycloalkyl, wherein said substituent is carboxyl,
  (8) unsubstituted or substituted phenyl wherein said substituent is one or more of carboxyl, carboxyalkyl or SO$_3$H,
  (9) unsubstituted or substituted amino, wherein said substituent is unsubstituted or substituted alkyl where said substituent is one or more of carboxyl, alkylsulfonyl or unsubstituted 5-membered heterocyclic rings having 1 or 2 heteroatoms, where said heteroatom is N,
  (10) unsubstituted or substituted heterocyclic rings selected from the group consisting of: pyrrolidinyl, imidazolyl, 1,2,4-triazolyl, tetrazolyl, tetrahydrofuranyl, furanyl, 1,3-dioxolanyl, thienyl, piperidinyl, piperazinyl, quinuclidinyl, morpholinyl, 1,3-tetrahydrothiazinyl, hexahydroazepinyl, tetrahydrothiopyranyl, 1-oxotetrahydrothiopyranyl and 1,1-dioxotetrahydrothiopyranyl wherein the linkage of the heterocyclic ring to the amidocarbonyl moiety can occur at a carbon atom or divalent nitrogen atom of the heterocyclic ring and wherein said substituent for any of said heterocyclic rings are one or more of alkyl, alkylcarbonyl, carboxyl, carboxyalkyl, carboxyaralkyl, aralkyl, aralkylcarbonyl, aralkoxycarbonyl, alkoxycarbonyl, alkoxycarbonylalkyl, aminoalkylcarbonyl, cyano, alkylsulfonyl, alkoxycarbonylaminoalkylcarbonyl, oxo or unsubstituted or substituted amino wherein said substituent is one or more of alkyl, carboxylalkyl, alkoxycarbonyl or alkoxycarbonylalkyl or
  (11) unsubstituted or substituted alkyl, wherein said substituent is one or more of hydroxyl, alkoxy, carboxyl, phenyl, hydroxyphenyl, alkylphenyl, carboxyalkylphenyl, cyano, alkylsulfonyl, acetamidino, formamidino, aminocarbonyl, alkylaminocarbonyl, aralkyl, aralkoxycarbonyl, halogen, thio, alkylthio, alkoxycarbonyl, alkoxycarbonylalkyl, Het, or unsubstituted or substituted amino, wherein said substituent is one or more of alkyl, deuterated alkyl, piperidinyl, Cyc, pyridinyl, morpholinyl, tetrahydropyranyl, tetrahydrothiapyranyl, tetrahydrothiapyranyl S-oxide, alkoxycarbonylpiperidinyl, cyano, cyanoalkyl, hydroxyalkyl, haloalkyl, dialkyl, alkylcarbonyl, carboxyl, alkylsulfonyl, carboxyalkyl, alkoxycarbonyl, alkoxycarbonylalkyl, aralkoxycarbonyl, aminoalkyl, aminocarbonyl, aminocarbonylalkyl, alkylaminocarbonyl, phenalkyl or unsubstituted or substituted alkylcarbonyl, where said substituent is a 5-membered heterocyclic ring having 1 or 2 heteroatoms and where said hetero atom is N, Cyc is defined as unsubstituted or substituted cycloalkyl wherein said substituent is alkoxycarbonyl, carboxyl, hydroxyl, oxo or spirodioxolanyl and Het is defined as unsubstituted or substituted heterocyclic rings selected from the group consisting of: pyrrolidinyl, imidazolyl, 1,2,4-triazolyl, tetrazolyl, tetrahydrofuranyl, furanyl, 1,3-dioxolanyl, thienyl, piperidinyl, piperazinyl, pyridinyl, quinuclidinyl, morpholinyl, 1,3-tetrahydrothiazinyl, hexahydroazepinyl, tetrahydropyranyl, tetrahydrothiopyranyl, 1-oxotetrahydrothiopyranyl and 1,1-dioxotetrahydrothiopyranyl wherein the linkage of the heterocyclic ring to the alkyl moiety can occur at a carbon atom or divalent nitrogen atom of the heterocyclic ring; and wherein said substituent for any of said heterocyclic rings are one or more of alkyl, amino, carboxyl, carboxyalkyl, aralkyl, carboxyaralkyl, alkoxycarbonyl, halogen substituted alkoxycarbonyl, alkoxycarbonylalkyl, alkoxyalkyl, alkoxyalkoxyalkyl, alkoxyalkoxyalkoxyalkyl, aralkylcarbonyl, aralkoxyalkyl, phenyl, aralkoxycarbonyl, oxo, SO$_3$H, or unsubstituted or substituted amino wherein said substituent is alkyl, carboxyl, carboxyalkyl, alkoxycarbonyl or alkoxycarbonylalkyl;
$R^{14}$ and $R^{15}$ are independently
  (1) hydrogen,
  (2) unsubstituted or substituted alkyl where said substituent is one or more of hydrogen, carboxyl, amino, aminoalkylamino, aminocarbonyl, hydroxyl, alkoxyl, alkylthio, thioalkyl, alkylsulfinyl, alkylsulfonyl, phenylalkoxycarbonyl, alkoxycarbonyl, indolyl, phenalkyl, hydroxyphenalkyl or unsubstituted 5-membered saturated heterocyclic rings having 1 or 2 hetero atoms wherein said hetero atom is N or (3) heterocyclic rings selected from the group consisting of: unsubstituted or substituted saturated or unsaturated rings having 5, 6, 7 or 8 total members and 1, 2, 3 or 4 N heteroatoms; having 5 or 6 total members and 1 or 2 O heteroatoms; having 5 or 6 total members and 1 S heteroatom; or having 6 total members and 2 different heteroatoms from the group consisting of N, O or S and wherein said substituent is one or more of alkyl, oxo, carboxyl, phenylalkyl, carboxyphenylalkyl or alkoxycarbonyl; and m and n are integers of from 0 to 1; and the pharmaceutically acceptable salts thereof.

23. The method of claim 22, wherein the compound has the formula

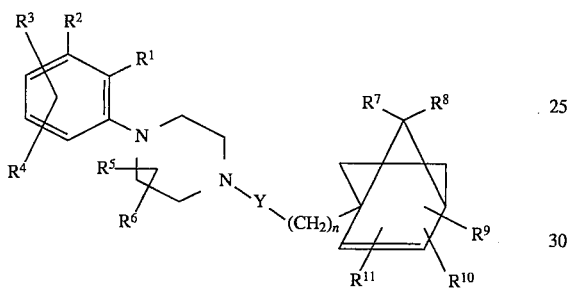

wherein $R^{11}$ is (1) —N($R^{12}$)—CO—$R^{13}$ or (2) —CO—N($R^{14}$)—$R^{15}$; and $R^{13}$ is (1) hydrogen,
(2) alkoxyl,
(3) aralkoxyl,
(4) carboxyl,
(5) alkoxycarbonyl,
(6) alkoxycarbonylamino,
(7) unsubstituted or substituted cycloalkyl, wherein said substituent is carboxyl,
(8) unsubstituted or substituted phenyl wherein said substituent is one or more of carboxyl, carboxyalkyl or SO$_3$H,
(9) unsubstituted or substituted amino, wherein said substituent is unsubstituted or substituted alkyl where said substituent is one or more of carboxyl, alkylsulfonyl or unsubstituted 5-membered heterocyclic rings having 1 or 2 heteroatoms, where said heteroatom is N,
(10) unsubstituted or substituted heterocyclic rings selected from the group consisting of: pyrrolidinyl, imidazolyl, 1,2,4-triazolyl, tetrazolyl, tetrahydrofuranyl, furanyl, 1,3-dioxolanyl, thienyl, piperidinyl, piperazinyl, quinuclidinyl, morpholinyl, 1,3-tetrahydrothiazinyl, hexahydroazepinyl, tetrahydrothiopyranyl, 1-oxotetrahydrothiopyranyl and 1,1-dioxotetrahydrothiopyranyl wherein the linkage of the heterocyclic ring to the amidocarbonyl moiety can occur at a carbon atom or divalent nitrogen atom of the heterocyclic ring and wherein said substituent for any of said heterocyclic rings are one or more of alkyl, alkylcarbonyl, carboxyl, carboxyalkyl, carboxyaralkyl, aralkyl, aralkylcarbonyl, aralkoxycarbonyl, alkoxycarbonyl, alkoxycarbonylalkyl, aminoalkylcarbonyl, cyano, alkylsulfonyl, alkoxycarbonylaminoalkylcarbonyl, oxo or unsubstituted or substituted amino wherein said substituent is one or more of alkyl, carboxyalkyl, alkoxycarbonyl or alkoxycarbonylalkyl or

(11) unsubstituted or substituted alkyl, wherein said substituent is one or more of hydroxyl, alkoxy, carboxyl, phenyl, hydroxyphenyl, alkylphenyl, carboxyalkylphenyl, cyano, alkylsulfonyl, acetamidino, formamidino, aminocarbonyl, alkylaminocarbonyl, aralkyl, aralkoxycarbonyl, halogen, thio, alkylthio, alkoxycarbonyl, alkoxycarbonylalkyl, Het, or unsubstituted or substituted amino, wherein said substituent is one or more of alkyl, deuterated alkyl, piperidinyl, Cyc, pyridinyl, morpholinyl, tetrahydropyranyl, tetrahydrothiapyranyl, tetrahydrothiapyranyl S-oxide, alkoxycarbonylpiperidinyl, cyano, cyanoalkyl, hydroxyalkyl, haloalkyl, dialkyl, alkylcarbonyl, carboxyl, alkylsulfonyl, carboxyalkyl, alkoxycarbonyl, alkoxycarbonylalkyl, aralkoxycarbonyl, aminoalkyl, aminocarbonyl, aminocarbonylalkyl, alkylaminocarbonyl, phenalkyl or unsubstituted or substituted alkylcarbonyl, where said substituent is a 5-membered heterocyclic ring having 1 heteroatom and where said heteroatom is N; Cyc is defined as unsubstituted or substituted cycloalkyl wherein said substituent is alkoxycarbonyl, carboxyl, hydroxyl, oxo or spiro-dioxolanyl and Het is defined as unsubstituted or substituted heterocyclic rings selected from the group consisting of: pyrrolidinyl, imidazolyl, 1,2,4-triazolyl, tetrazolyl, tetrahydrofuranyl, furanyl, 1,3-dioxolanyl, thienyl, piperidinyl, piperazinyl, pyridinyl, quinuclidinyl, morpholinyl, 1,3-tetrahydrothiazinyl, hexahydroazepinyl, tetrahydropyranyl, tetrahydrothio-pyranyl, 1-oxotetrahydrothiopyranyl and 1,1-dioxotetrahydrothiopyranyl wherein the linkage of the heterocyclic ring to the alkyl moiety can occur at a carbon atom or divalent nitrogen atom of the heterocyclic ring; and wherein said substituent for any of said heterocyclic rings are one or more of alkyl, amino, carboxyl, carboxyalkyl, aralkyl, carboxyaralkyl, alkoxycarbonyl, halogen substituted alkoxycarbonyl, alkoxycarbonylalkyl, alkoxyalkyl, alkoxyalkoxyalkyl, alkoxyalkoxyalkoxyalkyl, aralkylcarbonyl, aralkoxyalkyl, phenyl, aralkoxycarbonyl, oxo, SO$_3$H, or unsubstituted or substituted amino wherein said substituent is alkyl, carboxyl, carboxyalkyl, alkoxycarbonyl or alkoxycarbonylalkyl.

24. The method of claim 23, further comprising monitoring the neonate after delivery during the daylight hours.

25. The method of claim 24, wherein the compound has the formula

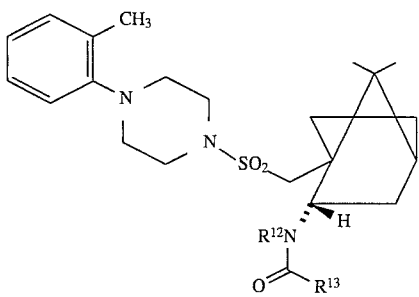

wherein $R^{12}$ is
(1) hydrogen,
(2) alkoxycarbonyl or
(3) unsubstituted of substituted alkyl wherein said substituent is hydroxyl, alkoxyl, carboxyl, carboxyalky, alkylsulfonyl or alkoxycarbonyl;

$R^{13}$ is
(1) hydrogen,
(2) alkoxyl,
(3) aralkoxyl,
(4) alkoxycarbonyl,
(5) alkoxycarbonylamino,
(6) unsubstituted or substituted cycloalkyl, wherein said substituent is carboxyl,
(7) unsubstituted or substituted phenyl wherein said substituent is one or more of carboxyl, carboxyalkyl or $SO_3H$,
(8) unsubstituted or substituted amino, wherein said substituent is unsubstituted or substituted alkyl where said substituent is one or more of carboxyl, alkylsulfonyl or unsubstituted 5-membered heterocyclic rings having 1 heteroatom, where said heteroatom is N,
(9) unsubstituted or substituted heterocyclic rings of the Formulae

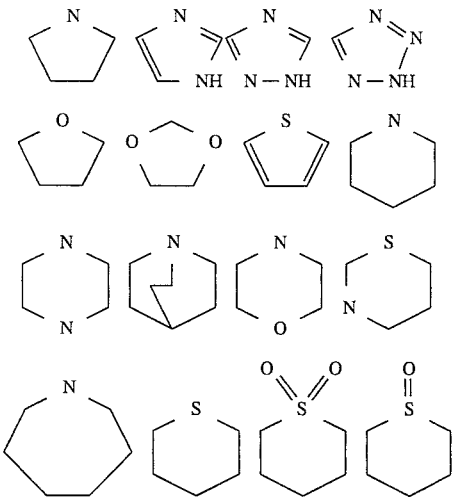

wherein the linkage of the heterocyclic ring to the amidocarbonyl moiety can occur at a carbon atom or divalent nitrogen atom of the heterocyclic ring and where said substituents on said heterocyclic ring are one or more of alkyl, carboxyl, carboxyalkyl, carboxyaralkyl, aralkylcarbonyl, aralkoxycarbonyl, alkoxycarbonyl, alkoxycarbonylalkyl, alkoxycarbonylaminoalkylcarbonyl, oxo or unsubstituted or substituted amino wherein said substituent is one or more of alkyl, carboxyalkyl, alkoxycarbonyl or alkoxycarbonylalkyl or

(10) unsubstituted or substituted alkyl, wherein said substituent is one or more of hydroxyl, carboxyl, carboxyalkylphenyl, alkylsulfonyl, aminocarbonyl, alkylaminocarbonyl, aralkyl, aralkoxycarbonyl, halogen, alkoxycarbonyl, alkoxycarbonylalkyl, Het or unsubstituted or substituted amino, wherein said substituent is one or more of alkyl, deuterated alkyl, cyanoalkyl, hydroxyalkyl, haloalkyl, dialkyl, alkylcarbonyl, alkylsulfonyl, carboxyalkyl, aminoalkyl, Cyc, piperidinyl, alkoxycarbonylpiperidinyl, pyridinyl, tetrahydropyranyl, tetrahydrothiopyranyl, tetrahydrothiopyranyl S-oxide, alkoxycarbonyl, alkoxycarbonylalkyl, aralkoxycarbonyl, aminocarbonylalkyl, alkylaminocarbonyl, phenalkyl or unsubstituted or substituted alkylcarbonyl, where said substituent is a 5-membered heterocyclic ring having 1 heteroatom and where said hetero atom is N, where Cyc is defined as substituted or unsubstituted cycloalkyl wherein said substituent is alkoxycarbonyl, Carboxyl, hydroxyl, oxo or spiro-dioxolanyl and Het is defined as unsubstituted or substituted heterocyclic rings of the Formulae

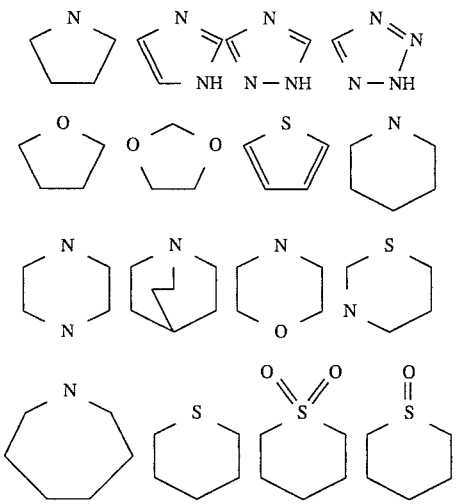

wherein the linkage of the heterocyclic ring to the alkyl moiety can occur at a carbon atom or divalent nitrogen atom of the heterocyclic ring and where said substituent on said heterocyclic ring is one or more of alkyl, amino, carboxyl, carboxyalkyl, carboxyaralkyl, alkoxycarbonyl, halogen substituted alkoxycarbonyl, alkoxycarbonylalkyl, alkoxyalkoxyalkyl, alkoxyalkoxyalkoxyalkyl, aralkylcarbonyl, aralkoxyalkyl, aralkoxyalkyl, aralkoxycarbonyl, oxo, $SO_3H$, or unsubstituted or substituted amino wherein said substituent is alkyl, carboxyalkyl, alkoxycarbonyl or alkoxycarbonylalkyl.

26. The method of claim 25, wherein
$R^{12}$ is
(1) hydrogen, or
(2) unsubstituted alkyl; and
$R^{13}$ is
(1) aralkoxyl, (2) unsubstituted or substituted heterocyclic rings of the Formulae

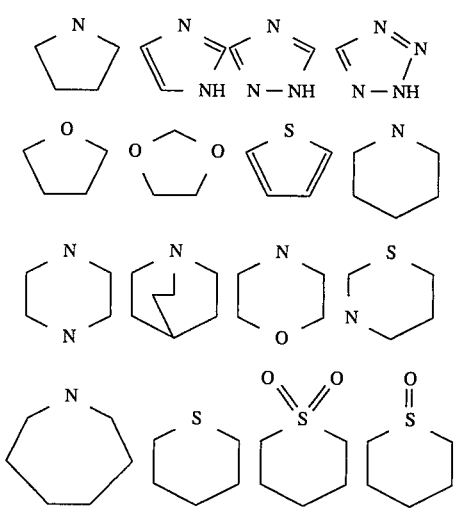

wherein the linkage of the heterocyclic ring to the amidocarbonyl moiety can occur at a carbon atom or divalent nitrogen atom of the heterocyclic ring and where said substituents on said heterocyclic ring are one or more of alkyl, carboxyl, carboxyalkyl, carboxyaralkyl, aralkylcarbonyl, aralkoxycarbonyl, alkoxycarbonyl, alkoxycarbonylalkyl, alkoxycarbonylaminoalkylcarbonyl, oxo or unsubstituted or substituted amino wherein said substituent is one or more of alkyl, carboxylalkyl, alkoxycarbonyl or alkoxycarbonylalkyl or (3) unsubstituted or substituted alkyl, wherein said substituent is one or more of hydroxyl, alkylsulfonyl, Het or unsubstituted or substituted amino, wherein said substituent is one or more of alkyl, deuterated alkyl, cyanoalkyl, hydroxyalkyl, haloalkyl, dialkyl, alkylcarbonyl, alkylsulfonyl, carboxyalkyl, aminoalkyl, Cyc, piperidinyl, alkoxycarbonylpiperidinyl, pyridinyl, tetrahydropyranyl, tetrahydrothiopyranyl, tetrahydrothiopyranyl S-oxide, alkoxycarbonyl or alkoxycarbonylalkyl; where Cyc is defined as substituted or unsubstituted cycloalkyl wherein said substituent is alkoxycarbonyl, carboxyl, and Het is defined as unsubstituted or substituted heterocyclic rings of the Formulae

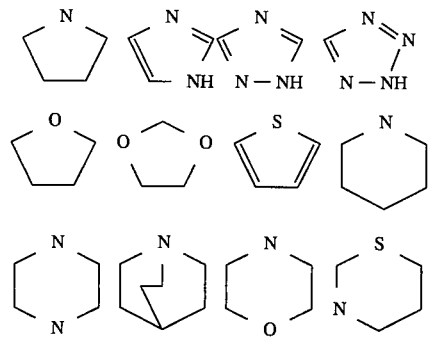

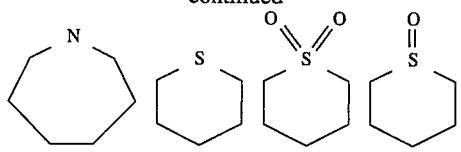

wherein the linkage of the heterocyclic ring to the alkyl moiety can occur at a carbon atom or divalent nitrogen atom of the heterocyclic ring and where said substituent on said heterocylcic ring is one or more of alkyl, amino, carboxyl, carboxyalkyl, carboxyaralkyl, alkoxycarbonyl, halogen substituted alkoxycarbonyl, alkoxycarbonylalkyl, alkoxyalkoxyalkyl, alkoxyalkoxyalkoxyalkyl, aralkylcarbonyl, aralkoxyalkyl, aralkoxyalkyl, aralkoxycarbonyl, oxo, SO₃H, or unsubstituted or substituted amino wherein said substituent is alkyl, carboxyalkyl, alkoxycarbonyl or alkoxycarbonylalkyl.

27. The method of claim 26, wherein the compound is

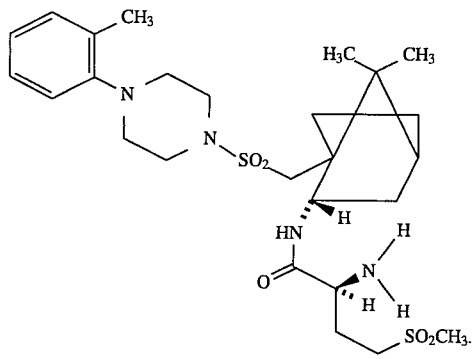

28. The method of claim 24, wherein the compound is administered at a daily dosage of 1 to 100 mg/kg.

29. The method of claim 28, wherein the daily dosage is 1 to 20 mg/kg.

30. The method of claim 28, wherein the compound is administered orally to the farm animal on the evening before delivery is expected.

31. The method of claim 27, wherein the compound is administered at a daily dosage of 1 to 100 mg/kg.

32. The method of claim 31, wherein the compound is administered orally to the farm animal on the evening before delivery is expected.

33. A method of controlling the timing of estrus in a farm animal, comprising administering to the farm animal a pharmacologically effective amount of a compound of formula I

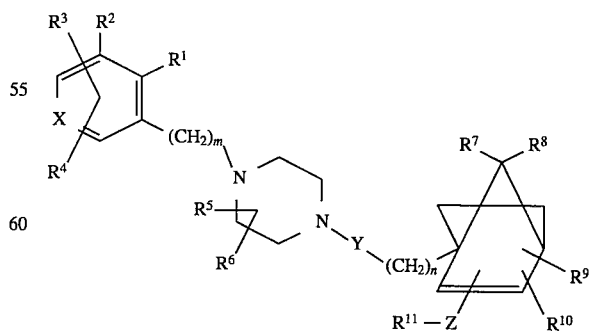

wherein
X is
(1) C or (2) N;

Y is
(1) carbonyl or
(2) sulfonyl;

Z is an optional substituent that, when present, is substituted or unsubstituted alkyl where said substituent is carboxyl;

$R^1$ is
(1) hydrogen,
(2) alkyl or
(3) $NH_2$;

$R^2$ is hydrogen, or $R^1$ and $R^2$ together are bridged alkyl of three or four methylenes;

$R^3$ and $R^4$ are independently one or more of
(1) hydrogen,
(2) halogen,
(3) alkylsulfonyl,
(4) alkoxy or
(5) unsubstituted or substituted alkyl wherein said substituent is hydroxyl, alkoxyl, alkylsulfonyl, amino, alkylamino or dialkylamino;

$R^5$ and $R^6$ are independently selected from
(1) hydrogen,
(2) alkyl,
(3) substituted alkyl where said substituent is amino, hydroxyl, alkoxyl, alkylsulfonyl, arylsulfonyl, alkylamino or dialkylamino,
(4) phenylalkyl or
(5) oxo;

$R^7$ and $R^8$ are independently one or more of
(1) hydrogen,
(2) alkyl or
(3) joined together to form unsubstituted or substituted cycloalkyl where said substituent is hydroxy or hydroxyalkyl;

$R^9$ and $R^{10}$ are independently selected from
(1) hydrogen,
(2) hydroxyl,
(3) halogen,
(4) oximino,
(5) methyl,
(6) carboxyl,
(7) oxo,
(8) alkoxycarbonyl,
(9) alkylcarbonyloxy,
(10) alkoxycarbonylalkoxy,
(11) trihaloalkylsulfonyloxo or
(12) unsubstituted or substituted amino where said substituent is one or more of alkyl, carboxyalkyl or alkoxycarbonylalkyl; or $R^9$ and $R^{10}$ are together joined to form a cyclic epoxide, whereby the $R^9$ and $R^{10}$ substituents are on the same carbon or on adjacent carbon atoms;

$R^{11}$ is
(1) hydrogen,
(2) —N($R^{12}$)—CO—$R^{13}$ or
(3) —CO—N($R^{14}$)—$R^{15}$;

$R^{12}$ is
(1) hydrogen,
(2) alkoxy,
(3) unsubstituted or substituted alkyl where said substituent is one or more of carboxyl, hydroxyl, alkoxyl, alkoxycarbonyl, alkylsulfonyl or arylsulfonyl,
(4) alkoxycarbonyl,
(5) alkoxycarbonylamino or
(6) alkylsulfonylalkyl;

$R^{13}$ is
(1) hydrogen,
(2) alkoxyl,
(3) aralkoxyl,
(4) carboxyl,
(5) alkoxycarbonyl,
(6) alkoxycarbonylamino,
(7) unsubstituted or substituted cycloalkyl, wherein said substituent is carboxyl,
(8) unsubstituted or substituted phenyl wherein said substituent is one or more of carboxyl, carboxyalkyl or $SO_3H$,
(9) unsubstituted or substituted amino, wherein said substituent is unsubstituted or substituted alkyl where said substituent is one or more of carboxyl, alkylsulfonyl or unsubstituted 5-membered heterocyclic rings having 1 or 2 heteroatoms, where said heteroatom is N,
(10) unsubstituted or substituted heterocyclic rings selected from the group consisting of: pyrrolidinyl, imidazolyl, 1,2,4-triazolyl, tetrazolyl, tetrahydrofuranyl, furanyl, 1,3-dioxolanyl, thienyl, piperidinyl, piperazinyl, quinuclidinyl, morpholinyl, 1,3-tetrahydrothiazinyl, hexahydroazepinyl, tetrahydrothiopyranyl, 1-oxotetrahydrothiopyranyl and 1,1-dioxotetrahydrothiopyranyl wherein the linkage of the heterocyclic ring to the amidocarbonyl moiety can occur at a carbon atom or divalent nitrogen atom of the heterocyclic ring and wherein said substituent for any of said heterocyclic rings are one or more of alkyl, alkylcarbonyl, carboxyl, carboxyalkyl, carboxyaralkyl, aralkyl, aralkylcarbonyl, aralkoxycarbonyl, alkoxycarbonyl, alkoxycarbonylalkyl, aminoalkylcarbonyl, cyano, alkylsulfonyl, alkoxycarbonyl-aminoalkylcarbonyl, oxo or unsubstituted or substituted amino wherein said substituent is one or more of alkyl, carboxyalkyl, alkoxycarbonyl or alkoxycarbonylalkyl or
(11) unsubstituted or substituted alkyl, wherein said substituent is one or more of hydroxyl, alkoxy, carboxyl, phenyl, hydroxyphenyl, alkylphenyl, carboxyalkylphenyl, cyano, alkylsulfonyl, acetamidino, formamidino, aminocarbonyl, alkylaminocarbonyl, aralkyl, aralkoxycarbonyl, halogen, thio, alkylthio, alkoxycarbonyl, alkoxycarbonylalkyl, Het, or unsubstituted or substituted amino, wherein said substituent is one-or more of alkyl, deuterated alkyl, piperidinyl, Cyc, pyridinyl, morpholinyl, tetrahydropyranyl, tetrahydrothiapyranyl, tetrahydrothiapyranyl S-oxide, alkoxycarbonylpiperidinyl, cyano, cyanoalkyl, hydroxyalkyl, haloalkyl, dialkyl, alkylcarbonyl, carboxyl, alkylsulfonyl, carboxyalkyl, alkoxycarbonyl, alkoxycarbonylalkyl, aralkoxycarbonyl, aminoalkyl, aminocarbonyl, aminocarbonylalkyl, alkylaminocarbonyl, phenalkyl or unsubstituted or substituted alkylcarbonyl, where said substituent is a 5-membered heterocyclic ring having 1 or 2 heteroatoms and where said heteroatom is N, Cyc is defined as unsubstituted or substituted cycloalkyl wherein said substituent is alkoxycarbonyl, carboxyl, hydroxyl, oxo or spirodioxolanyl and Het is defined as unsubstituted or substituted heterocyclic rings selected from the group consisting of: pyrrolidinyl, imidazolyl, 1,2,4- triazolyl, tetrazolyl, tetrahydrofuranyl, furanyl, 1,3-dioxolanyl, thienyl, piperidinyl, piperazinyl, pyridinyl, quinuclidinyl, morpholinyl, 1,3-tetrahydrothiazinyl, hexahydroazepinyl, tetrahydropyranyl, tetrahydrothiopyranyl, 1-oxotetrahydrothiopyranyl and 1,1-dioxotetrahydrothiopyranyl wherein the linkage of the heterocyclic ring to the alkyl moiety can occur at a carbon atom or divalent nitrogen atom of the heterocyclic ring; and wherein said substituent for any of said heterocyclic rings are one or more of alkyl, amino, carboxyl, carboxyalkyl, aralkyl, carboxyaralkyl, alkoxycarbonyl, halogen substituted alkoxycarbonyl, alkoxycarbonylalkyl, alkoxyalkyl, alkoxyalkoxyalkyl, alkoxyalkoxyalkoxyalkyl, aralkylcarbonyl, aralkoxyalkyl, phenyl, aralkoxycarbonyl, oxo, $SO_3H$, or unsubstituted or substituted amino wherein said substituent is alkyl, carboxyl, carboxyalkyl, alkoxycarbonyl or alkoxycarbonylalkyl;

$R^{14}$ and $R^{15}$ are independently
  (1) hydrogen,
  (2) unsubstituted or substituted alkyl where said substituent is one or more of hydrogen, carboxyl, amino, aminoalkylamino, aminocarbonyl, hydroxyl, alkoxyl, alkylthio, thioalkyl, alkylsulfinyl, alkylsulfonyl, phenylalkoxycarbonyl, alkoxycarbonyl, indolyl, phenalkyl, hydroxyphenalkyl or unsubstituted 5-membered saturated heterocyclic rings having 1 or 2 hetero atoms wherein said hetero atom is N or
  (3) heterocyclic rings selected from the group consisting of: unsubstituted or substituted saturated or unsaturated rings having 5, 6, 7 or 8 total members and 1, 2, 3 or 4 N heteroatoms; having 5 or 6 total members and 1 or 2 O heteroatoms; having 5 or 6 total members and 1 S heteroatom; or having 6 total members and 2 different heteroatoms from the group consisting of N, O or S and wherein said substituent is one or more of alkyl, oxo, carboxyl, phenylalkyl, carboxyphenylalkyl or alkoxycarbonyl; and m and n are integers of from 0 to 1; and the pharmaceutically acceptable salts thereof.

34. The method of claim 33, wherein the compound has the formula

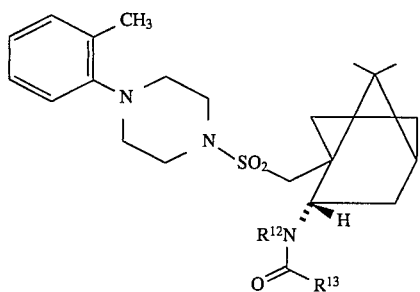

wherein
$R^{12}$ is
  (1) hydrogen,
  (2) alkoxycarbonyl or
  (3) unsubstituted of substituted alkyl wherein said substituent is hydroxyl, alkoxyl, carboxyl, carboxyalky, alkylsulfonyl or alkoxycarbonyl;
$R^{13}$ is
  (1) hydrogen,
  (2) alkoxyl,
  (3) aralkoxyl,
  (4) alkoxycarbonyl,
  (5) alkoxycarbonylamino,
  (6) unsubstituted or substituted cycloalkyl, wherein said substituent is carboxyl,
  (7) unsubstituted or substituted phenyl wherein said substituent is one or more of carboxyl, carboxyalkyl or $SO_3H$,
  (8) unsubstituted or substituted amino, wherein said substituent is unsubstituted or substituted alkyl where said substituent is one or more of carboxyl, alkylsulfonyl or unsubstituted 5-membered heterocyclic rings having 1 or 2 heteroatoms, where said heteroatom is N,
  (9) unsubstituted or substituted heterocyclic rings of the Formulae

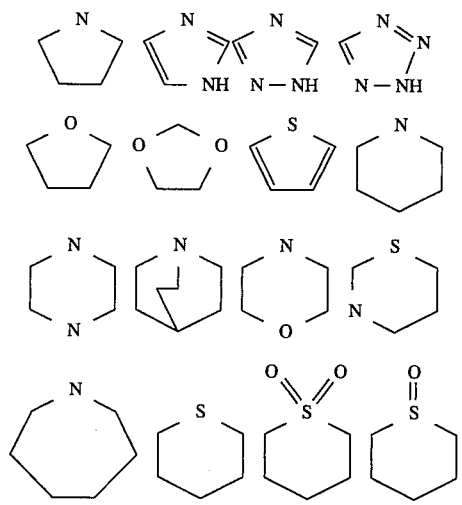

wherein the linkage of the heterocyclic ring to the amidocarbonyl moiety can occur at a carbon atom or divalent nitrogen atom of the heterocyclic ring and where said substituents on said heterocyclic ring are one or more of alkyl, carboxyl, carboxyalkyl, carboxyaralkyl, aralkylcarbonyl, aralkoxy-carbonyl, alkoxycarbonyl, alkoxycarbonylalkyl, alkoxy-carbonylaminoalkylcarbonyl, oxo or unsubstituted or substituted amino wherein said substituent is one or more of alkyl, carboxylalkyl, alkoxycarbonyl or alkoxycarbonylalkyl or
  (10) unsubstituted or substituted alkyl, wherein said substituent is one or more of hydroxyl, carboxyl, carboxyalkylphenyl, alkylsulfonyl, aminocarbonyl, alkylaminocarbonyl, aralkyl, aralkoxycarbonyl, halogen, alkoxycarbonyl, alkoxycarbonylalkyl, Het or unsubstituted or substituted amino, wherein said substituent is one or more of alkyl, deuterated alkyl, cyanoalkyl, hydroxyalkyl, haloalkyl, dialkyl, alkylcarbonyl, alkylsulfonyl, carboxyalkyl, aminoalkyl, Cyc, piperidinyl, alkoxycarbonylpiperidinyl, pyridinyl, tetrahydropyranyl, tetrahydrothiopyranyl, tetrahydrothiopyranyl S-oxide, alkoxycarbonyl, alkoxycarbonylalkyl, aralkoxycarbonyl, aminocarbonylalkyl, alkylaminocarbonyl, phenalkyl or unsubstituted or substituted alkylcarbonyl, where said substituent is a 5-membered heterocyclic ring having 1 heteroatom and where said hetero atom is N, where Cyc is defined as substituted or unsubstituted cycloalkyl wherein said substituent is alkoxycarbonyl, carboxyl, hydroxyl, oxo or spiro-dioxolanyl and Het is defined as unsubstituted or substituted heterocyclic rings of the Formulae

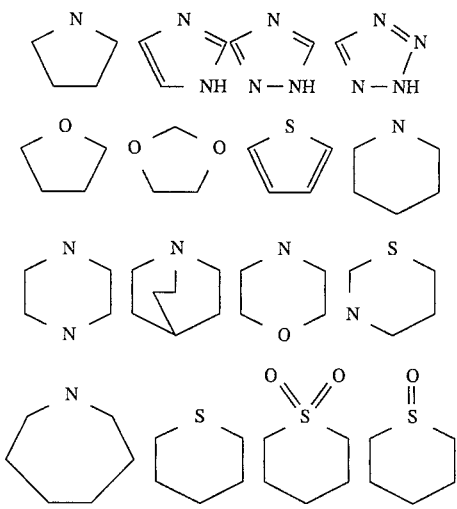

wherein the linkage of the heterocyclic ring to the alkyl moiety can occur at a carbon atom or divalent nitrogen atom of the heterocyclic ring and where said substituent on said heterocyclic ring is one or more of alkyl, amino, carboxyl, carboxyalkyl, carboxyaralkyl, alkoxycarbonyl, halogen substituted alkoxycarbonyl, alkoxycarbonylalkyl, alkoxyalkoxyalkyl, alkoxyalkoxyalkoxyalkyl, aralkylcarbonyl, aralkoxyalkyl, aralkoxyalkyl, aralkoxycarbonyl, oxo, $SO_3H$, or unsubstituted or substituted amino wherein said substituent is alkyl, carboxyalkyl, alkoxycarbonyl or alkoxycarbonylalkyl.

35. The method of claim 33, wherein administration of the compound begins prior to expected estrus.

36. The method of claim 34, wherein the compound is administered orally to the farm animal at a daily dosage of 1 to 100 mg/kg.

* * * * *